(12) United States Patent
Furuhashi

(10) Patent No.: US 11,045,360 B2
(45) Date of Patent: Jun. 29, 2021

(54) UNDERPANTS-TYPE DISPOSABLE DIAPER

(71) Applicant: Daio Paper Corporation, Ehime (JP)

(72) Inventor: Yukina Furuhashi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 514 days.

(21) Appl. No.: 16/082,736

(22) PCT Filed: Feb. 24, 2017

(86) PCT No.: PCT/JP2017/007003
§ 371 (c)(1),
(2) Date: Sep. 6, 2018

(87) PCT Pub. No.: WO2017/169381
PCT Pub. Date: Oct. 5, 2017

(65) Prior Publication Data
US 2019/0083327 A1    Mar. 21, 2019

(30) Foreign Application Priority Data

Mar. 30, 2016  (JP) .............................. JP2016-069129

(51) Int. Cl.
*A61F 13/491* (2006.01)
*A61F 13/496* (2006.01)
(Continued)

(52) U.S. Cl.
CPC .......... *A61F 13/4915* (2013.01); *A61F 13/49* (2013.01); *A61F 13/491* (2013.01);
(Continued)

(58) Field of Classification Search
CPC .. A61F 13/4915; A61F 13/49; A61F 13/4902; A61F 13/491; A61F 13/496; A61F 13/532
See application file for complete search history.

(56) References Cited

U.S. PATENT DOCUMENTS 5,567,501 A * 10/1996 Srinivasan ............. D04H 1/558
                                                       428/137
5,851,935 A * 12/1998 Srinivasan ............. B32B 5/022
                                                       442/328
(Continued)

FOREIGN PATENT DOCUMENTS

EP    3202383    *  8/2017  .......... A61F 13/496
EP    3251644    * 12/2017  ............ A61F 13/15
(Continued)

OTHER PUBLICATIONS

International Search Report, PCT/JP2017/007003, dated May 30, 2017.

*Primary Examiner* — Michele M Kidwell
(74) *Attorney, Agent, or Firm* — Andrus Intellectual Property Law, LLP

(57) ABSTRACT

A fitting to a male genitalia has a male-genitalia-facing portion. Portions on both sides thereof in a width direction, in an outer member of a front body, have an elastic film stretchable structure in which an elastic film is stacked between a first sheet layer and a second sheet layer, which are bonded by sheet bonded portions arranged at intervals. A change region is included in which an area rate of the bonded portions decreases stepwise or continuously from a central portion of the male-genitalia-facing portion in a width direction to the portions of the both sides of the male-genitalia-facing portion in the width direction. A portion of the change region other than a portion having the highest area rate of the bonded portions, is contracted in the width direction due to contraction of the elastic film in a natural length state and is extensible in the width direction.

8 Claims, 15 Drawing Sheets

(51) Int. Cl.
  *A61F 13/532*  (2006.01)
  *A61F 13/49*  (2006.01)
(52) U.S. Cl.
  CPC .......... *A61F 13/496* (2013.01); *A61F 13/532*
       (2013.01); *A61F 13/4902* (2013.01)

(56) References Cited

U.S. PATENT DOCUMENTS

| | | | |
|---|---|---|---|
| 2002/0016122 A1* | 2/2002 | Curro ....................... | B29C 55/18 |
| | | | 442/381 |
| 2004/0209042 A1* | 10/2004 | Peacock ................ | A61F 13/512 |
| | | | 428/136 |
| 2010/0163161 A1* | 7/2010 | Gilgenbach ....... | A61F 13/49017 |
| | | | 156/155 |
| 2010/0215923 A1* | 8/2010 | Frost ....................... | B32B 27/12 |
| | | | 428/196 |
| 2013/0102982 A1 | 4/2013 | Nakano et al. | |
| 2014/0130956 A1 | 5/2014 | Floberg et al. | |
| 2018/0008481 A1 | 1/2018 | Takahashi et al. | |
| 2018/0014979 A1* | 1/2018 | Fujita ................ | B29C 66/81429 |
| 2018/0014984 A1* | 1/2018 | Sakai .................... | B29C 66/344 |
| 2018/0028371 A1* | 2/2018 | Takaishi ............ | A61F 13/51464 |
| 2018/0078429 A1* | 3/2018 | Matsumura ........... | A61F 13/496 |
| 2018/0338872 A1* | 11/2018 | Takahashi ......... | A61F 13/51104 |
| 2018/0344540 A1* | 12/2018 | Oshima ................ | A61F 13/533 |
| 2019/0046367 A1* | 2/2019 | Oshima ................ | A61F 13/534 |
| 2019/0060140 A1* | 2/2019 | Oshima ........... | A61F 13/49426 |
| 2019/0167487 A1* | 6/2019 | Takeuchi ................ | B29C 66/41 |
| 2019/0254885 A1* | 8/2019 | Takeuchi ............... | A61F 13/496 |
| 2020/0397626 A1* | 12/2020 | Sakai ................. | B29C 66/1122 |

FOREIGN PATENT DOCUMENTS

| | | | | |
|---|---|---|---|---|
| EP | 3254654 | * | 12/2017 | ............. A61F 13/49 |
| JP | 1029259 | | 9/2004 | |
| JP | 2004261331 | | 9/2004 | |
| JP | 2004532758 | | 10/2004 | |
| JP | 200797621 | | 4/2007 | |
| JP | 2010273842 | | 12/2010 | |
| JP | 201210905 | | 1/2012 | |
| JP | 4934835 | | 5/2012 | |
| JP | 2014520589 | | 8/2014 | |
| WO | 2013002691 | | 1/2013 | |
| WO | 2016121976 | | 8/2016 | |
| WO | 2016158932 | | 10/2016 | |

* cited by examiner

UNDERPANTS-TYPE DISPOSABLE DIAPER

CROSS-REFERENCE TO RELATED APPLICATIONS

This application is the U.S. national stage application of International Application PCT/JP2017/007003, filed Feb. 24, 2017, which international application was published on Oct. 5, 2017, as International Publication WO 2017/169381 in the Japanese language. The International Application claims priority of Japanese Patent Application No. 2016-069129, filed Mar. 30, 2016. The international application and Japanese application are both incorporated herein by reference, in entirety.

TECHNICAL FIELD

The present invention relates to an underpants-type disposable diaper excellent in fitting to male genitalia.

BACKGROUND ART

In general, an underpants-type disposable diaper includes an outer member disposed in a front body and a back body provided individually or as one unit and an inner member, which includes an absorber and is fixed to an internal surface of the outer member from the front body to the back body, and both side edge portions of the outer member in the front body and both side edge portions of the outer member in the back body are bonded to form side seal portions, thereby forming a waist opening and a pair of left and right leg openings.

In general, the outer member has a lower torso region defined as a range in a front-back direction having the side seal portions (a range in the front-back direction from the waist opening to upper ends of the leg openings) and an intermediate region defined as a range of a portion forming the leg openings in the front-back direction, the intermediate region has covering regions located on the both sides of the inner member, and elastic members such as thread rubbers or elastic sheets are provided in the lower torso region or the covering regions (for example, see Patent Literatures 1 and 2).

However, in the conventional underpants-type disposable diaper, there is room for improvement in fitting to male genitalia. That is, in the outer member of the conventional underpants-type disposable diaper, an elastically stretchable member is not provided in a male-genitalia-facing portion or a contraction force uniformly acts in a width direction even when at least one elastically stretchable member is provided. Thus, in the former case, the male-genitalia-facing portion becomes loose-fitting and is likely to influence a silhouette of clothing. In addition, in the latter case, the male genitalia are pressed.

CITATION LIST

Patent Literature

Patent Literature 1: JP 2012-10905 A
Patent Literature 2: JP 4934835 B2
Patent Literature 3: JP 2004-532758 A

SUMMARY OF INVENTION

Technical Problem

In this regard, a main object of the invention is to improve fitting to male genitalia.

Solution to Problem

Representative aspects of the invention solving the above-mentioned problem are as follows.
<First Aspect>
An underpants-type disposable diaper comprising:
an outer member disposed in a front body and a back body provided individually or as one unit;
an inner member fixed to the outer member from the front body to the back body, the inner member including an absorber, side seal portions at which both side edge portions of the outer member in the front body and both side edge portions of the outer member in the back body are bonded together, a waist opening, and a pair of left and right leg openings, wherein
at least a male-genitalia-facing portion and portions on both sides thereof in a width direction, in the outer member of the front body, have an elastic film stretchable structure in which an elastic film is stacked between a first sheet layer and a second sheet layer and the first sheet layer and the second sheet layer are bonded directly or indirectly by a plurality of sheet bonded portions arranged at intervals, and
the outer member of the front body has a change region in which an area rate of the bonded portions decreases stepwise or continuously from a central portion of the male-genitalia-facing portion in the width direction to the portions on the both sides of the male-genitalia-facing portion in the width direction, and at least a portion of the change region other than a portion having the highest area rate of the bonded portions, is contracted in the width direction due to contraction of the elastic film in a natural length state and is extensible in the width direction.
(Operational Advantage)
In the elastic film stretchable structure described above, basically, as the area rate of the bonded portions increases, a portion decreases in which the first sheet layer and the second sheet layer contract by the elastic film, and elongation at an elastic limit decreases. Therefore, when the area rate of the bonded portions decreases stepwise or continuously from the central portion of the male-genitalia-facing portion in the width direction to the both sides of the male-genitalia-facing portion in the width direction, the male-genitalia-facing portion bulges outward in the natural length state, and bulging is maintained even in the worn state of being stretched to some extent. Furthermore, besides mere bulging, at least the portion other than the portion having the highest area rate of the bonded portions has extensibility, and thus loose-fitting rarely occurs. Therefore, fitting to the male genitalia is remarkably improved.
<Second Aspect>
The underpants-type disposable diaper according to the first aspect, wherein
the elastic film stretchable structure is, in the outer member of the front body, provided at least throughout a range including the male-genitalia-facing portion and a peripheral portion thereof, and
the change region is a region in which the area rate of the bonded portions decreases stepwise or continuously from the central portion of the male-genitalia-facing portion to the peripheral portion of the male-genitalia-facing portion.

(Operational Advantage)

In this way, excellent fitting can be obtained to wrap the whole bulging of the male genitalia.

<Third Aspect>

The underpants-type disposable diaper according to the first or second aspect, wherein the absorber is obtained by mixing and accumulating pulp fibers and superabsorbent polymer particles, and a basis weight of the absorber decreases stepwise or continuously according to a decrease in the area rate of the bonded portions in the change region in a portion overlapping the change region.

(Operational Advantage)

It is preferable to increase a basis weight of the absorber to ensure the amount of urine absorption in the male-genitalia-facing portion. However, since the male-genitalia-facing portion of the invention corresponds to a stretchable region, when the basis weight is increased entirely in the male-genitalia-facing portion, there is concern that flexibility may be impaired, deformation may become difficult, and fitting may be degraded. On the other hand, when the basis weight decreases stepwise or continuously according to a decrease in the area rate of the bonded portions in the change region in the portion in which the absorber overlaps with the change region, it is possible to ensure the basis weight, that is, the amount of absorption of the absorber without degrading fitting.

<Fourth Aspect>

The underpants-type disposable diaper according to any one of the first to third aspects, wherein the elastic film stretchable structure is provided throughout a range from a portion on one side of the inner member to a portion on the other side of the inner member in the width direction, the change region is provided within a range in a width direction of the inner member, and a lowest area rate of the bonded portions in the change region is lower than an area rate of the bonded portions in a region outside the change region.

(Operational Advantage)

In this way, when the change region in which the area rate of the bonded portions is changed such that fitting of the male-genitalia-facing portion is improved, is provided within the width direction range of the inner member, and the area rate in the change region and the area rate in the region on the outside the change region has the above-described relationship, the amount of contraction increases stepwise or continuously from the central portion of the change region toward the outside thereof and from the outside of the change region toward the change region, and thus fitting around a bulging portion at the male-genitalia-facing portion is improved.

Advantageous Effects of Invention

As described above, the invention has advantages such as compatibility between fitting to intergluteal cleft and fitting to a site adjacent to both sides of the intergluteal cleft in a width direction, etc.

DESCRIPTION OF EMBODIMENTS

Figure 1:
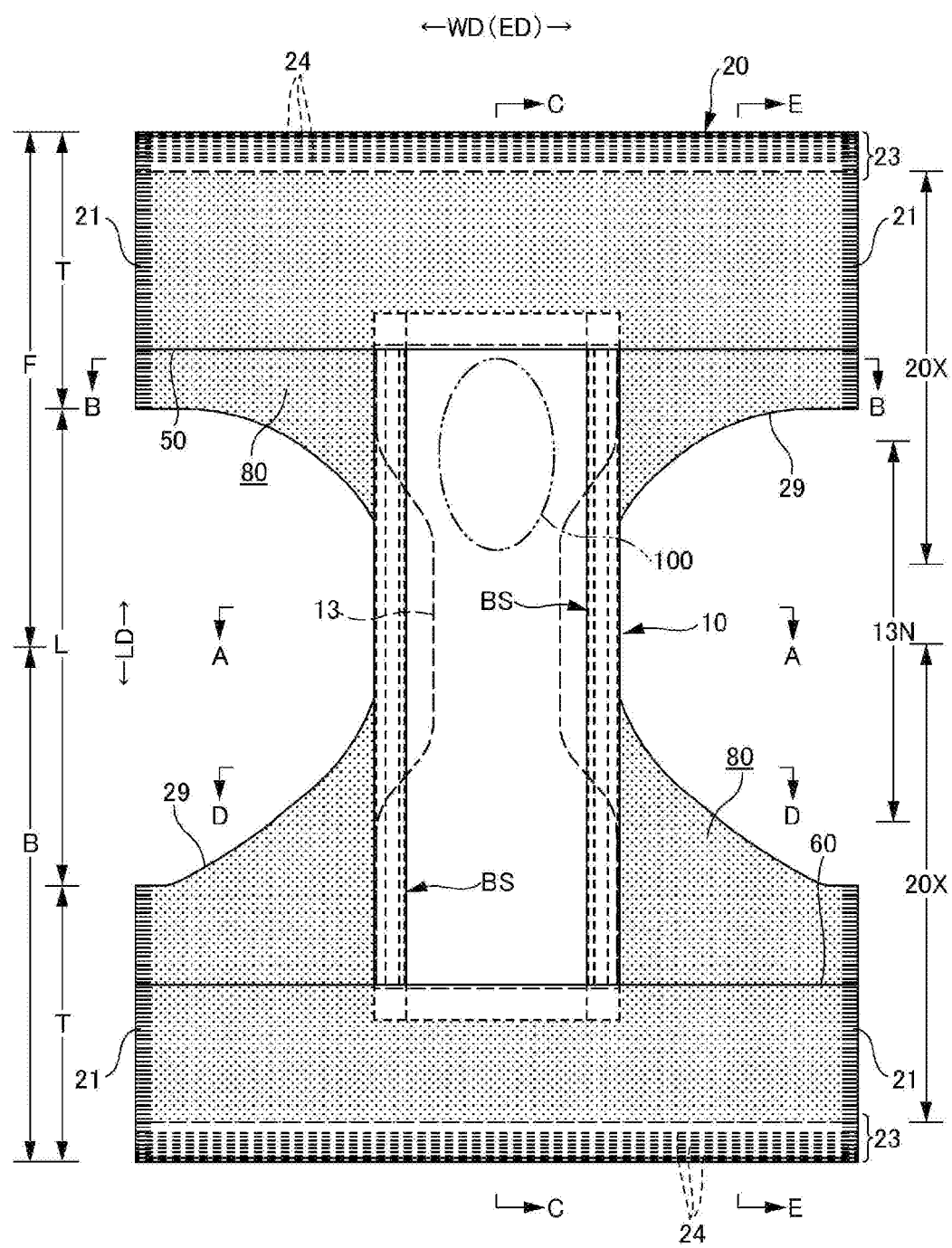
FIG. 1 is a plan view (internal surface side) of an underpants-type disposable diaper in a completely spread state.

Hereinafter, an embodiment of the invention will be described in detail with reference to accompanying drawings. A dotted portion in a cross-sectional view indicates bonding means such as a hot-melt adhesive.

FIG. 1 to FIG. 7 illustrate an underpants-type disposable diaper. This underpants-type disposable diaper (hereinafter also simply referred to as a diaper) has an outer member 20 disposed in a front body F and a back body B provided as one unit and an inner member 10 attached to an internal surface of the outer member 20 as one unit. Further, in the inner member 10, an absorber 13 is interposed between a liquid pervious top sheet 11 disposed on a front surface side and a liquid impervious sheet 12 disposed on a back surface side. In manufacturing, after a back surface of the inner member 10 is bonded to the internal surface of the outer member 20 using bonding means such as a hot-melt adhesive (a pattern part 10B of FIG. 7), the inner member 10 and the outer member 20 are folded at a center in a front-back direction LD corresponding to a boundary between the front body F and the back body B, and both side portions thereof are bonded to each other by heat sealing, a hot-melt adhesive, etc. to form a side seal portion 21, thereby obtaining an underpants-type disposable diaper in which a waist opening and a pair of left and right leg openings are formed.

(Exemplary Structure of Inner Member)

Figure 4:
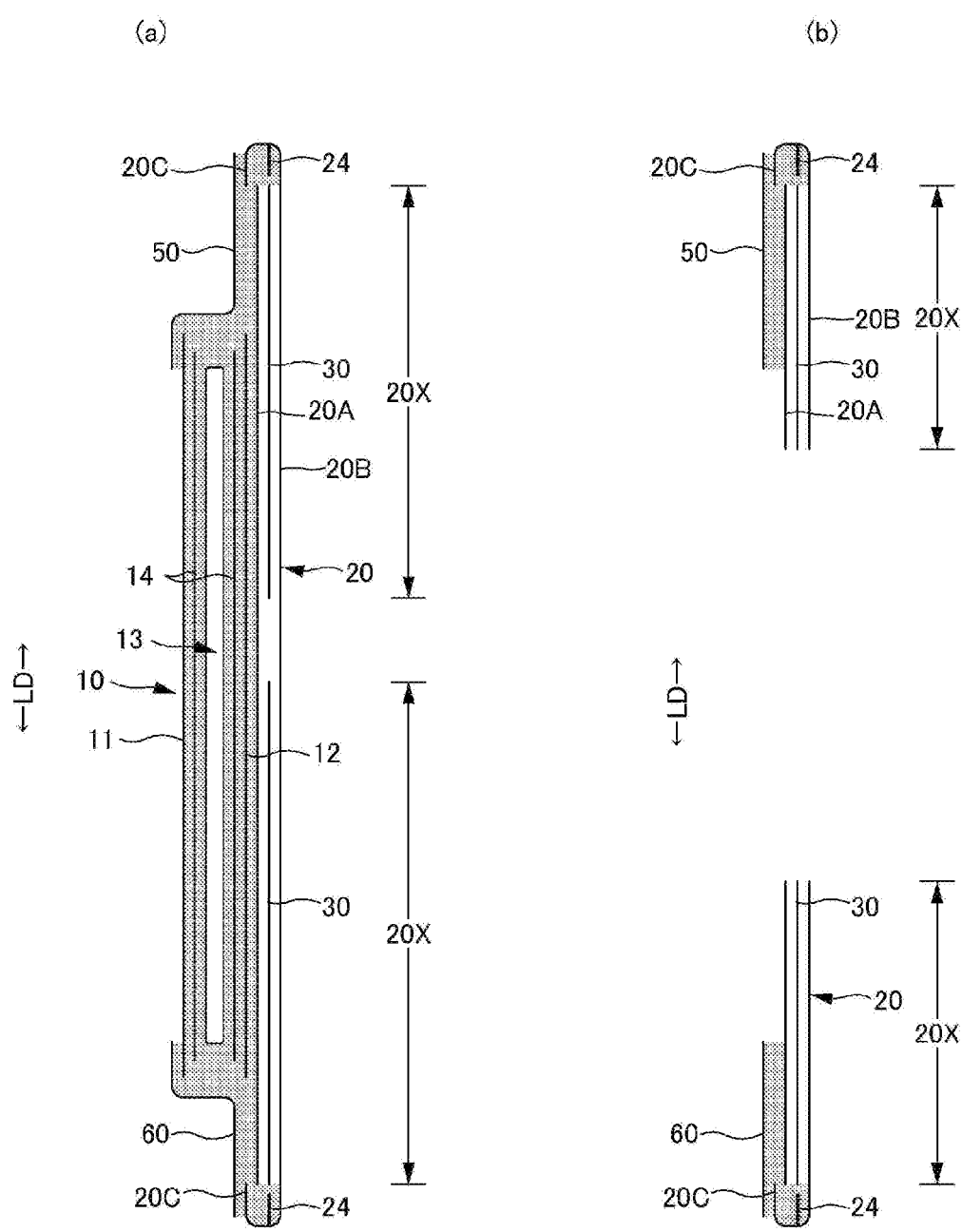
FIG. 4(a) is a C-C cross-sectional view of FIG. 1.
FIG. 4(b) is an E-E cross-sectional view of FIG. 1.
Figure 5:
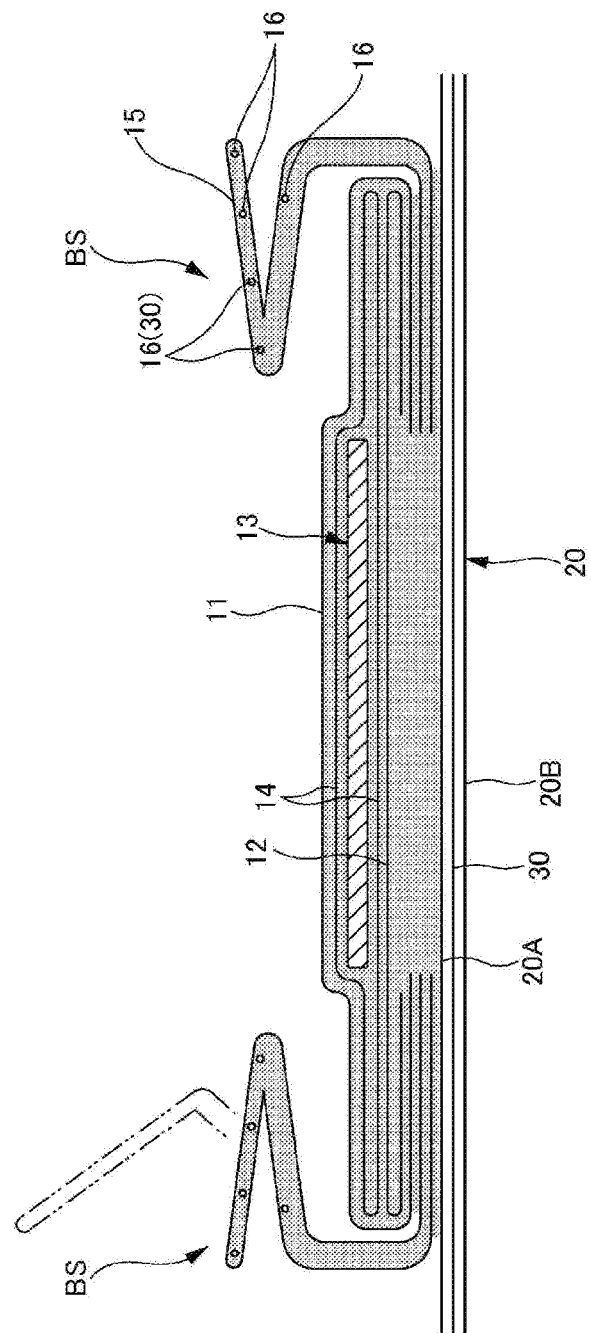
FIG. 5 is an A-A cross-sectional view of FIG. 1.
Figure 6:
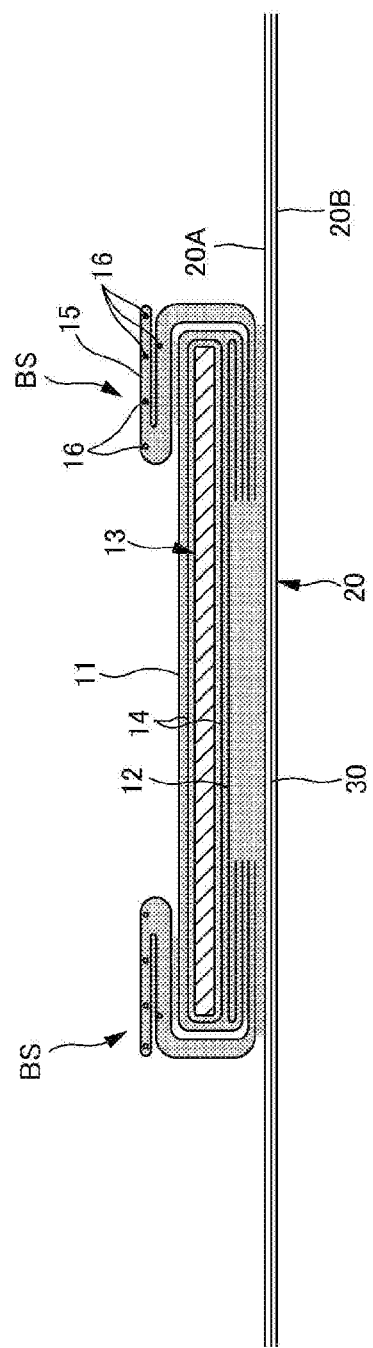
FIG. 6 is a B-B cross-sectional view of FIG. 1.

As illustrated in FIGS. 4 to 6, the inner member 10 has a structure in which the absorber 13 is interposed between the top sheet 11 made of a nonwoven fabric, etc. and the liquid impervious sheet 12 made of polyethylene, etc., and absorbs and retains excretory fluid passing through the top sheet 11. The inner member 10 may have any planar shape and typically has a substantially rectangular shape as in an illustrated aspect.

The top sheet 11 that covers a front surface side (skin contact surface side) of the absorber 13 is suitably made of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of flexibility and drape characteristics and thermal bonding in view of bulky soft products. A large number of through-holes formed in the top sheet 11 facilitates absorption of urine and achieves dry touch characteristics. The top sheet 11 extends around side edge portions of the absorber 13 and extends to the back surface side of the absorber 13.

A liquid impervious plastic sheet such as polyethylene sheet or polypropylene sheet is used as the liquid impervious sheet 12 that covers the back surface side (non-skin contact surface side) of the absorber 13. Recently, permeable sheets have been preferably used in view of preventing stuffiness. This water-block permeable sheet is a micro-porous sheet prepared through melt-kneading an olefin resin, for example, polyethylene resin or polypropylene resin, and inorganic filler, forming a sheet with the kneaded materials, and then uniaxially or biaxially stretching the sheet.

The absorber 13 may be composed of a well-known basic component, such as an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-permeable and liquid-retainable wrapping sheet 14, such as a crepe sheet, to retain the shape and polymers, as required.

The absorber 13 has a substantially hourglass shape having, at a crotch portion, a narrowing part 13N whose width is narrower than that of both front and back sides. However, it is possible to adopt an appropriate shape such as a rectangular shape. The size of the narrowing part 13N may be appropriately determined. A length of the narrowing part 13N in the front-back direction LD may be set to about 20 to 50% of the entire length of the diaper, and a width of a narrowest part thereof may be set to about 40 to 60% of the entire width of the absorber 13. If the inner member 10 has a substantially rectangular planar shape in the case of the absorber with such a narrowing part 13N, the inner member 10 has non-absorber side portions free of the absorber 13 according to the narrowing part 13N of the absorber 13.

Three-dimensional gathers BS, which are configured to fit around the legs, are formed at both side portions of the inner member 10. As illustrated in FIG. 5 and FIG. 6, each of the three-dimensional gathers BS includes a fixed portion fixed to a side portion of the back surface of the inner member, a main body portion extending from the fixed portion around the side of the inner member to the side portion of the front surface of the inner member, fallen portions formed by fixing the front end portion and back end portion of the main body portion to the side portion of the front surface of the inner member in a fallen state, and a free part formed in an un-fixed state between the fallen portions. The three-dimensional gathers BS are each composed of a gather sheet 15 obtained by folding a sheet such as a nonwoven fabric into a duplicate sheet.

In addition, elongated gather elastic members 16 are disposed, for example, at a tip portion of the free part, between double sheets. As indicated by a two-dot chain line in FIG. 5, the gather elastic members 16 form the three-dimensional gather BS by erecting the free part using an elastic stretching force in a product state.

The liquid impervious sheet 12 is folded back to the back surface side together with the top sheet 11 at both sides of the absorber 13 in the width direction WD. It is desirable that the liquid impervious sheet 12 is opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the top sheet 11, the gather nonwoven fabric 15 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. It is desirable that the gather nonwoven fabric 15 is a water-repellent nonwoven fabric coated with a water repellent agent, for example, a silicone-based agent, a paraffin-metallic agent, or an alkyl chromic chloride agent to prevent permeability of urine, etc., to prevent diaper rash, and to enhance feeling to skin (dryness).

Figure 7:
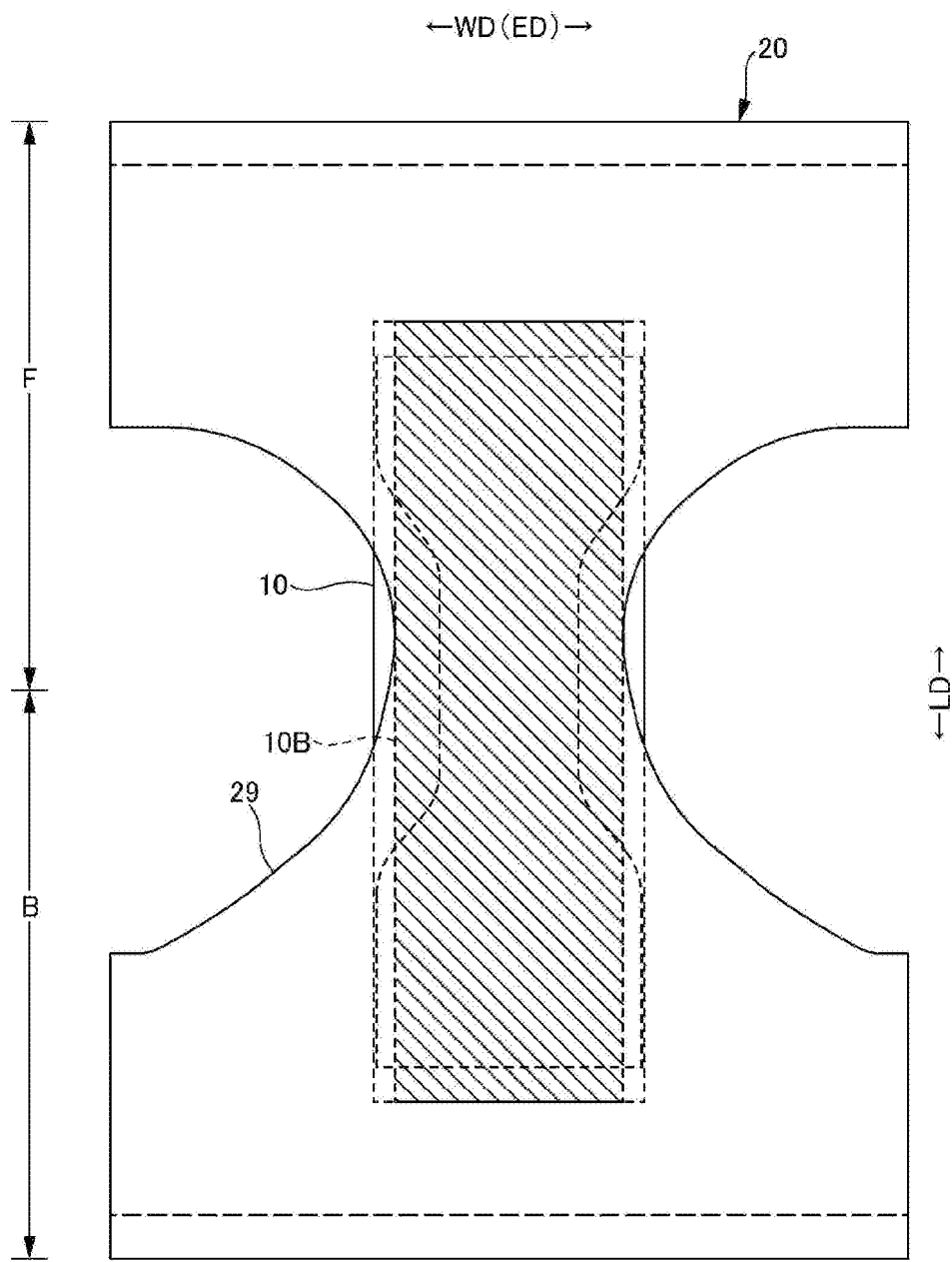
FIG. 7 is a plan view illustrating only a main part of the underpants-type disposable diaper in the completely spread state.

As illustrated in FIG. 7, the back surface of the inner member 10 is fixed to the internal surface of the outer member 20 by a hot-melt adhesive, etc. in an internal and external fixed region 10B (shaded area). It is more preferable that the internal and external fixed region 10B is fixed to the outer member 20 throughout substantially the entire part in the width direction WD and the substantially the entire part in the front-back direction LD in the inner member 10. However, the internal and external fixed region 10B may be non-bonded at the both side portions of the inner member, etc.

(Front and Back Cover Sheets)

As illustrated in FIG. 1 and FIG. 4, front and back cover sheets 50 and 60 may be provided to cover the front and back ends of the inner member 10 attached to the internal surface of the outer member 20 and to prevent leakage from the front and back edges of the inner member 10. The illustrated mode will be described in more detail. The front cover sheet 50 extends along the entire part in the width direction WD from an internal surface of a folded part 20C of a waist side end portion to a position overlapping with a front end portion of the inner member 10 on the internal surface of the front body F. The back cover sheet 60 extends along the entire part in the width direction WD from the internal surface of a folded part 20C of a waist side end portion to a position overlapping with a back end portion of the inner member 10 on the internal surface of the back body B. Minor non-bonded portions may be provided along the entire part in the width direction WD (or only at a central portion) at edge portions of the front and back cover sheets 50 and 60 on the crotch side. The front and back cover sheets 50 and 60 having such non-bonded portions can prevent leakage of the adhesive, and function as barriers against leakage when slightly suspended from the top sheet.

As in the illustrated mode, when the front and back cover sheets 50 and 60 are attached as separate components, there is an advantage that a range of choice of material is enlarged. However, there is a disadvantage that materials and manufacturing processes increase. Thus, the folded parts 20C formed by folding back the outer member 20 toward the inner surface of the diaper may be respectively extended to portions overlapping with the inner member 10 to have the same function as that of the cover sheets 50 and 60.

(Structure Example of Outer Member)

The outer member 20 of the illustrated mode forms the front body F and the back body B as one unit, and has a lower torso region T defined as a range of the side seal portion 21 in the front-back direction LD in which the front body F and the back body B are bonded together and an intermediate region L defined as a range of a portion forming leg openings in the front-back direction LD. Further, in the outer member 20 of the illustrated mode, except for the middle of the intermediate portion L in the front-back direction LD, an elastic film 30 is stacked between a first sheet layer 20A and a second sheet layer 20B, as illustrated in FIG. 2 and FIG. 4 to FIG. 6, and the first sheet layer 20A and the second sheet layer 20B have an elastic film stretchable structure 20X, a stretchable direction of which is the width direction, bonded at a large number of sheet bonded portions 40 arranged at intervals as illustrated in FIG. 3. A planar shape of the outer member 20 is formed including a concave-shaped leg lines 29 such that both side edges of the intermediate portion L in the width direction WD form the leg openings, and corresponds to a shape similar to an hourglass as a whole. The outer member 20 may be divided into two front and back parts, and the both parts may be separated from each other in the front-back direction LD at the crotch portion.

In addition, in the outer member 20, as illustrated in FIG. 4, the elastic film 30 and elongated elastic members 24 extending along the width direction WD are provided between the first sheet layer 20A and the second sheet layer 20B, and elasticity is imparted in the width direction WD.

More specifically, waist portion elastic members 24 are provided in a waist portion 23 of the outer member 20. The waist portion elastic members 24 are elongated elastic members such as a plurality of rubber threads disposed at intervals in the front-back direction LD, and apply a stretching force to tighten around the waist of the body. The waist portion elastic members 24 are not disposed substantially as a bundle with a close spacing, but three or more, preferably five or more members are disposed at intervals of about 3 to 8 mm to form a predetermined stretchable zone. A stretch rate of the waist portion elastic member 24 in fixing may be appropriately determined. However, the stretch rate may be set to about 230 to 320% in the case of normal adult use.

In an illustrated example, thread rubbers are used as the waist portion elastic members 24. However, for example, tape-like elastic members may be used. Alternatively, the elastic film 30 described below may be extended to the waist portion 23. The waist portion elastic members 24 of the illustrated mode are interposed in the folded part 20C formed by folding a constituent material of the second sheet layer 20B toward the internal surface side at a waist opening edge. However, the waist portion elastic members 24 may be interposed between a constituent material of the first sheet layer 20A and the constituent material of the second sheet layer 20B.

A shape of each of the sheet bonded portions 40 and a shape of each of the through-holes 31 in a natural length state may be appropriately determined. However, it is possible to adopt an arbitrary shape such as a perfect circle, an ellipse, a polygon such as a triangle, a rectangle, a rhombus, etc., a convex lens shape, a concave lens shape, a star shape, a cloud shape, etc. The dimensions of each of the sheet bonded portions 40 are not particularly restricted. However, a maximum length is preferably set to 0.5 to 3.0 mm, particularly 0.7 to 1.1 mm, and a maximum width $40x$ is preferably set to 0.1 to 3.0 mm, particularly 0.1 to 1.1 mm in a case of a shape which is long in an orthogonal direction XD orthogonal to the stretchable direction ED.

A size of each of the sheet bonded portions 40 may be appropriately determined. However, when the size is excessively large, the hardness of the sheet bonded portions 40 has a significant influence on sense of touch. When the size is excessively small, a bonded area is small, and materials may not be sufficiently attached to each other. Thus, in general, an area of each of the sheet bonded portions 40 is preferably set to about 0.14 to 3.5 $mm^2$ (particularly about 0.25 to 1.0 $mm^2$). An area of an opening of each of the through-holes 31 may be greater than or equal to that of the sheet bonded portions since the sheet bonded portions are formed via the through-holes 31, and the area is preferably set to about 1 to 1.5 times the area of each of the sheet bonded portions. The area of the opening of each of the through-holes 31 refers to a value in a natural length state and in a state where the elastic film 30, the first sheet layer 20A and the second sheet layer 20B are provided in one unit, rather than a state of the elastic film 30 alone, and refers to a minimum value in a case in which the area of the opening of each of the through-holes 31 is not uniform in a thickness direction such as a case in which the area is different between a front and a back of the elastic film 30.

The planar geometries of the sheet bonded portions 40 and the through-holes 31 may be appropriately determined. Preferred is regularly repeated geometry, such as an oblique lattice shape illustrated in FIG. 15(a), a hexagonal lattice shape (these shapes are also referred to as a staggered shape) illustrated in FIG. 15(b), a square lattice shape illustrated in FIG. 15(c), a rectangular lattice shape illustrated in FIG. 15(d), a parallelotope lattice shape illustrated in FIG. 15(e) (a mode in which two groups are provided such that a large number of diagonally parallel arrays intersect each other, as shown in the drawings), etc. (including arrays tilted by less than 90 degrees with respect to stretchable direction ED). Alternatively, the sheet bonded portions 40 may be arrayed in regularly repeated groups (the geometry of each group may be regular or irregular, and may be in a pattern or characteristic letters). Arrangements of the bonded portions 40 and through-holes 31 may be the same in a plurality of regions having different area rates or different therebetween.

The bonding means of the first sheet layer 20A and the second sheet layer 20B in the bonded portions 40 is not particularly limited. For example, bonding of the first sheet layer 20A and the second sheet layer 20B in the bonded portions 40 may be performed by a hot-melt adhesive or performed by bonding means by material welding such as heat sealing or ultrasonic sealing. In addition, the first sheet layer 20A and the second sheet layer 20B may be bonded through the elastic film 30 or directly bonded via throughholes formed in the elastic film. In the latter case, it is desirable that neither the first sheet layer 20A nor the second sheet layer 20B is bonded to the elastic film 30 at least in a portion other than a portion between the first sheet layer 20A and the second sheet layer 20B in the sheet bonded portions 40.

Figure 8:
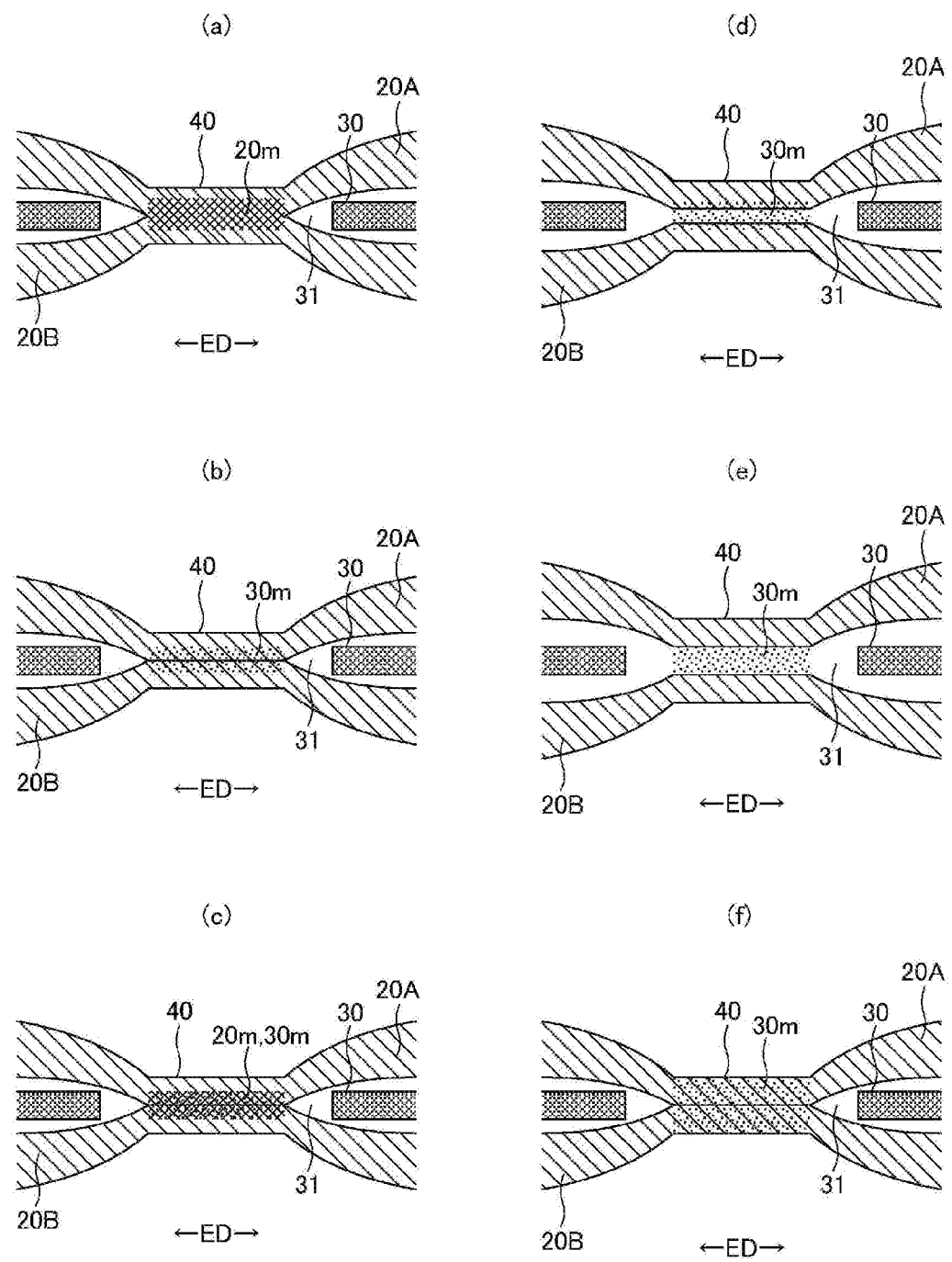
FIG. 8 is a cross-sectional view schematically illustrating a cross section of a main part of the outer member stretched to a certain extent in a width direction.

As a mode in which the sheet bonded portions 40 are formed by material welding, it is possible to adopt any one of a first welding mode (see FIG. 8(a)) in which the first sheet layer 20A and the second sheet layer 20B are bonded only by a melted and solidified material 20m corresponding to a most part or a part of at least one of the first sheet layer 20A and the second sheet layer 20B in the sheet bonded portions 40; a second welding mode (see FIG. 8(b)) in which the first sheet layer 20A and the second sheet layer 20B are bonded only by a melted and solidified material 30m corresponding to a whole, a most part, or a part of the elastic film 30 in the sheet bonded portions 40; and a third welding mode (see FIG. 8(c)) obtained by combining these welding modes, and it is preferable to adopt the second and third welding modes. A particularly preferable mode is a mode in which the first sheet layer 20A and the second sheet layer 20B are bonded by the melted and solidified material 20m corresponding to a part of the first sheet layer 20A and the second sheet layer 20B and the melted and solidified material 30m corresponding to a whole or a most part of the elastic film 30 in the sheet bonded portions 40.

In a case in which the first sheet layer 20A and the second sheet layer 20B are bonded using a melted and solidified material 20m corresponding to a most part or a part of at least one of the first sheet layer 20A and the second sheet layer 20B as an adhesive as in a first adhesion mode or a third adhesion mode, it is preferable that a part of the first sheet layer 20A and the second sheet layer 20B is not melted in order not to harden the sheet bonded portions 40. When the first sheet layer 20A and the second sheet layer 20B are nonwoven fabrics, a case in which a part of the first sheet layer 20A and the second sheet layer 20B is not melted includes a mode in which for all fibers of the sheet bonded portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

Peel strength becomes high when the first sheet layer 20A and the second sheet layer 20B are bonded using the melted and solidified material 30m of the elastic film 30 as an adhesive, as in the second welding mode and the third welding mode. In the second welding mode, under the condition that a melting point of at least one of the first sheet layer 20A and the second sheet layer 20B is higher than a melting point of the elastic film 30 and a heating temperature at the time of forming the sheet bonded portions 40, the elastic film 30 may be interposed between the first sheet layer 20A and the second sheet layer 20B, portions to be the sheet bonded portions 40 may be pressed and heated, and only the elastic film 30 may be melted to perform the welding. Meanwhile, in the third welding mode, under the condition that a melting point of at least one of the first sheet layer 20A and the second sheet layer 20B is higher than the melting point of the elastic film 30, the elastic film 30 may be interposed between the first sheet layer 20A and the second sheet layer 20B, the portions to be the sheet bonded portions 40 may be pressed and heated, and the elastic film 30 and at least one of the first sheet layer 20A and the second sheet layer 20B may be melted to perform the welding. From this point of view, the melting point of the elastic film 30 is preferably about 80 to 145° C., melting points of the first sheet layer 20A and the second sheet layer 20B are preferably about 85 to 190° C., particularly, about 150 to 190° C., and a difference between the melting points of the first sheet layer 20A and the second sheet layer 20B and the melting point of the elastic film 30 is preferably about 60 to 90° C. In addition, the heating temperature is preferably set to 100 to 150° C.

In the second welding mode and the third welding mode, when the first sheet layer 20A and the second sheet layer 20B are nonwoven fabrics, the melted and solidified material 30m of the elastic film 30 may infiltrate among fibers throughout the whole thickness direction of the first sheet layer 20A and the second sheet layer 20B of the sheet bonded portions 40 as illustrated in FIG. 8(f). However, flexibility of the sheet bonded portions 40 becomes high in a mode in which the melted and solidified material 30m infiltrates among fibers in the thickness direction halfway as illustrated in FIGS. 8(b), 8(c), and FIG. 8(d), or a mode in which the melted and solidified material 30m hardly infiltrates among the fibers of the first sheet layer 20A and the second sheet layer 20B as illustrated in FIG. 8(e).

Constituent materials of the first sheet layer 20A and the second sheet layer 20B are not particularly limited as long as the materials have sheet shapes, and a nonwoven fabric is preferably used in view of air permeability and flexibility. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 12 to approximately 20 g/m$^2$. The first sheet layer 20A and the second sheet layer 20B may be composed of a pair of facing layers prepared by folding back a single sheet that is partially or entirely folded back. For example, as in the illustrated mode, in the waist region 23, a component located outer side may be used as the second sheet layer 20B, the folded part 20C formed by folding back to the internal surface side at the waist opening edge thereof may be used as the first sheet layer 20A, and the elastic film 30 may be interposed therebetween, and in the rest part, a component located inner side may be used as the first sheet layer 20A, another component located outer side may be used as the second sheet layer 20B, and the elastic film 30 may be interposed therebetween. The component of the first sheet layer 20A and the component of the second sheet layer 20B may be respectively provided throughout the whole part in the front-back direction LD, and the elastic film 30 may be interposed between the component of the first sheet layer 20A and the component of the second sheet layer 20B without folding back the component members.

The elastic film 30 may be composed of any thermoplastic resin film having elasticity. For example, it is possible to use a film in which a large number of holes or a large number of slits is formed for ventilation in addition to a nonporous film. In particular, it is preferable when the elastic film 30 has a tensile strength in the width direction WD (the stretchable direction ED, the MD) of 8 to 25 N/35 mm, tensile strength in the front-back direction LD (the orthogonal direction XD orthogonal to the stretchable direction ED, the CD) of 5 to 20 N/35 mm, tensile elongation in the width direction WD of 450 to 1,050%, and tensile elongation in the front-back direction LD of 450 to 1,400%. The thickness of the elastic film 30 is not particularly restricted. However, the thickness is preferably in a range of about 20 to 40 μm. In addition, a basis weight of the elastic film 30 is not particularly limited. However, the basis weight is preferably about 30 to 45 g/m$^2$, and particularly preferably about 30 to 35 g/m$^2$.

(Stretchable Region)

A region having the elastic film stretchable structure 20X in the outer member 20 has a stretchable region 80 which is stretchable in the width direction WD. In a case of having a non-stretchable region described below, the entire portion other than the non-stretchable region is the stretchable region. In a case of not having the non-stretchable region, the entire elastic film stretchable structure is the stretchable region.

The stretchable region 80 has sections 32 in each of which the elastic film 30 linearly continues along the width direction WD. The stretchable region 80 is contracted in the width direction WD by a contraction force of the elastic film 30, and is extensible in the width direction WD. More specifically, in a state in which the elastic film 30 is stretched in the width direction WD, the first sheet layer 20A and the second sheet layer 20B are bonded via the through-holes 31 of the elastic film 30 at intervals in each of the width direction WD and the front-back direction LD orthogonal thereto (the orthogonal direction XD orthogonal to the stretchable direction ED), and the large number of sheet bonded portions 40 are formed, thereby forming the entire elastic film stretchable structure 20X including both the stretchable region 80 and the non-stretchable region 70. Further, in the stretchable region 80, it is possible to be extensible by arranging the through-holes 31 such that the stretchable region 80 has the sections in each of which the elastic film 30 linearly continues along the width direction WD.

Figure 14:
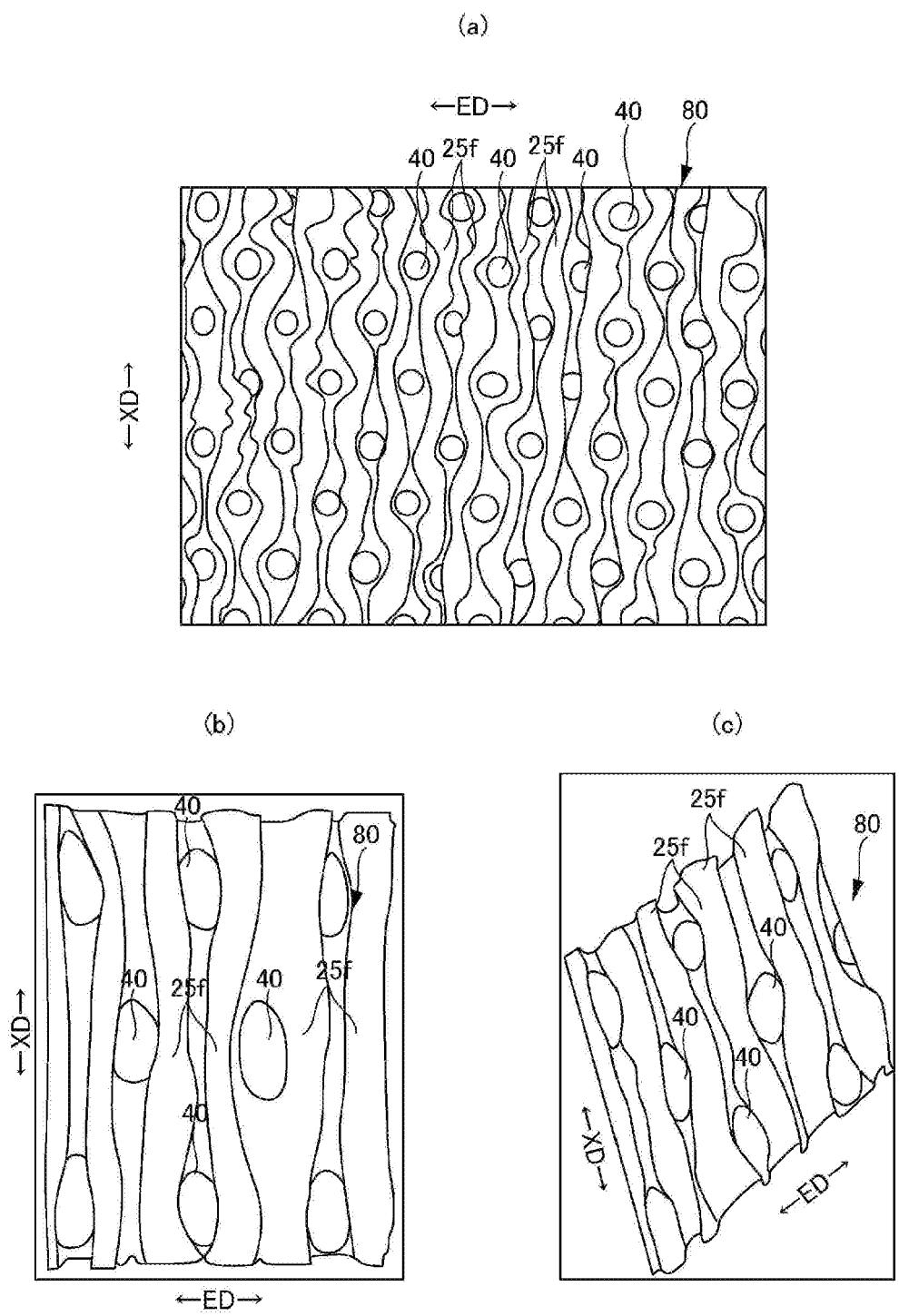
FIG. 14(a) is a trace diagram of a microscope photograph from a plane direction.
FIG. 14(b) is a trace diagram of a high-magnification microscope photograph from the plane direction.
FIG. 14(c) is a trace diagram of a high-magnification microscope photograph from an oblique direction in a stretchable region of a sample.

In the stretchable region 80, as illustrated in FIG. 3(d), in the natural length state of the elastic film 30, the first sheet layer 20A and the second sheet layer 20B between the two adjacent bonded portions 40 are raised in directions away from each other, and thus a contraction wrinkle 25 extending in a direction intersecting the stretchable direction ED is formed. Further, as illustrated in FIG. 3(c), even in a worn state stretched to some extent in the width direction WD, the contraction wrinkles 25 are still remained while being stretched. In addition, as in the illustrated mode, when neither the first sheet layer 20A nor the second sheet layer 20B is bonded to the elastic film 30 at least in the portion other than the portion between the first sheet layer 20A and the second sheet layer 20B in the sheet bonded portions 40, as is understood from FIG. 3(c) assuming the worn state and FIGS. 3(a) and 3(b) assuming the completely spread state of the first sheet layer 20A and the second sheet layer 20B, gaps are formed between the through-holes 31 in the elastic film 30 and the bonded portions 40 in these states, air permeability is imparted due to these gaps even when the material of the elastic film 30 is an imperforate film or an imperforate sheet. On the other hand, in the natural length state, the through-holes 31 are narrowed due to contraction of the elastic film 30, and almost no gap is formed between the through-holes 31 and the sheet bonded portions 40. States of the contraction wrinkle 25 in the worn state and in the natural length state are exemplified in FIG. 14.

It is desirable that an elongation at an elastic limit of the stretchable region 80 in the width direction WD is set to 200% or more (preferably 265% to 295%). The elongation at the elastic limit of the stretchable region 80 is substantially determined by the stretch rate of the elastic film 30 in the manufacturing. However, the elongation at the elastic limit decreases due to a factor that inhibits contraction in the width direction WD based thereon. A main inhibition factor corresponds to a ratio of the length 40x of the sheet bonded portions 40 to a unit length in the width direction WD. As this ratio increases, the elongation at the elastic limit decreases. In general, since the length 40x of each of the sheet bonded portions 40 correlates with the area rate of the sheet bonded portions 40, the elongation at the elastic limit of the stretchable region 80 may be adjusted by the area rate of the sheet bonded portions 40.

Stretching stress of the stretchable region 80 may be adjusted mainly by a sum of widths 32w of the sections 32 in each of which the elastic film 30 linearly continues along the width direction WD. The width 32w of the section 32 in which the elastic film 30 linearly continues along the width direction WD is equal to an interval 31d of the through-holes 31 in the front-back direction LD coming into contact with both side edges of the continuing section 32. The interval 31d of the through-holes 31 is equal to an interval 40d of the sheet bonded portions 40 in the front-back direction LD coming into contact with the both side edges of the continuing section when the length 31y of the through-hole 31 in the front-back direction LD is equal to the length 40y of the sheet bonded portion 40 in the front-back direction LD (for example, when a scheme of simultaneously forming the through-holes 31 and the sheet bonded portions 40 described above is adopted). Therefore, in this case, the stretching stress of the stretchable region 80 may be adjusted by a ratio of the length 40y of each of the sheet bonded portions 40 to a unit length in the front-back direction LD. In general, since the length 40y of each of the sheet bonded portions 40 correlates with the area rate of the sheet bonded portions 40, the stretching stress of the stretchable region 80 may be adjusted by the area rate of the sheet bonded portions 40. Stretching stress in stretching to 50% of an elastic limit may be estimated as the stretching stress of the stretchable region 80.

The area rate of the sheet bonded portions 40 and the area of each of the sheet bonded portions 40 in the stretchable region 80 may be appropriately determined. However, in general, the area rate and the areas are preferably set within the following ranges.

Area of each of sheet bonded portions 40: 0.14 to 3.5 mm$^2$ (particularly 0.14 to 1.0 mm$^2$)

Area rate of sheet bonded portions 40: 1.8 to 19.1% (particularly 1.8 to 10.6%)

(Non-Stretchable Region)

The region having the elastic film stretchable structure 20X may have the non-stretchable region 70. Arrangement of the non-stretchable region 70 may be appropriately determined. However, for example, in a region overlapping with the absorber 13 in the outer member 20 of the underpants-type disposable diaper, it is desirable that the elastic film 30 is disposed for a manufacturing reason. However, the region is a region in which extension and contraction are unnecessary. Therefore, it is preferable that a part or a whole of a portion overlapping with the absorber 13 (it is desirable to include substantially the entire internal and external fixed region 10B) in the region having the elastic film stretchable structure 20X is set as the non-stretchable region 70. It is as a matter of course possible to provide the non-stretchable region 70 with a range beyond the region overlapping with the absorber 13 to a region not overlapping with the absorber 13 located around the region overlapping with the absorber in the width direction WD or the front-back direction LD thereof, or it is possible to provide the non-stretchable region 70 only in the region not overlapping with the absorber 13. In the illustrated mode, since a region overlapping with the absorber 13 in the outer member 20 of the front body F is a region including the stretchable region 80 as described below, an entire portion overlapping with the absorber 13 in the outer member 20 of the back body B (it is desirable to include substantially the entire internal and external fixed region 10B) is set as the non-stretchable region 70.

The non-stretchable region 70 may be formed by thermally degrading the elastic film 30 or finely cutting the elastic film 30 in the width direction WD so that the contraction force of the elastic film 30 does not act, and may be formed by increasing the area rate of the sheet bonded portions 40. In particular, in a case in which the sheet bonded portions 40 are formed by bonding the first sheet layer 20A and the second sheet layer 20B via the through-holes penetrating the elastic film 30, it is preferable that the area rate of the sheet bonded portions 40 is increased so that the non-stretchable region is obtained by forming regions without any section in which the elastic film 30 continues in the width direction WD, due to the presence of through-holes 31, while the elastic film 30 is continuous along the width direction WD. In the non-stretchable region 70, the elastic film 30 does not linearly continue along the width direction WD. Thus, the contraction force of the elastic film 30 hardly acts on the first sheet layer 20A or the second sheet layer 20B, elasticity is almost lost, and the elongation at the elastic limit approaches 100%. Further, in the non-stretchable region 70, the first sheet layer 20A and the second sheet layer 20B are bonded by the large number of sheet bonded portions 40 arranged at intervals, and the sheet bonded portions 40 are discontinuous. Thus, a decrease in flexibility is prevented. In other words, it is possible to form the stretchable region 80 and the non-stretchable region 70 depending on the presence or absence of the portions in each of which the elastic film 30 does not linearly continue along the width direction WD. In addition, continuity of the elastic film 30 remains also in the non-stretchable region 70. Since any independent cut piece of the elastic film 30 is not left, and any wrinkle is not formed, appearance is extremely excellent, and air permeability in the thickness direction by the through-holes 31 is ensured. In the non-stretchable region 70, the elongation at the elastic limit in the width direction WD is preferably 120% or less (preferably 110% or less, more preferably 100%).

Figure 13:
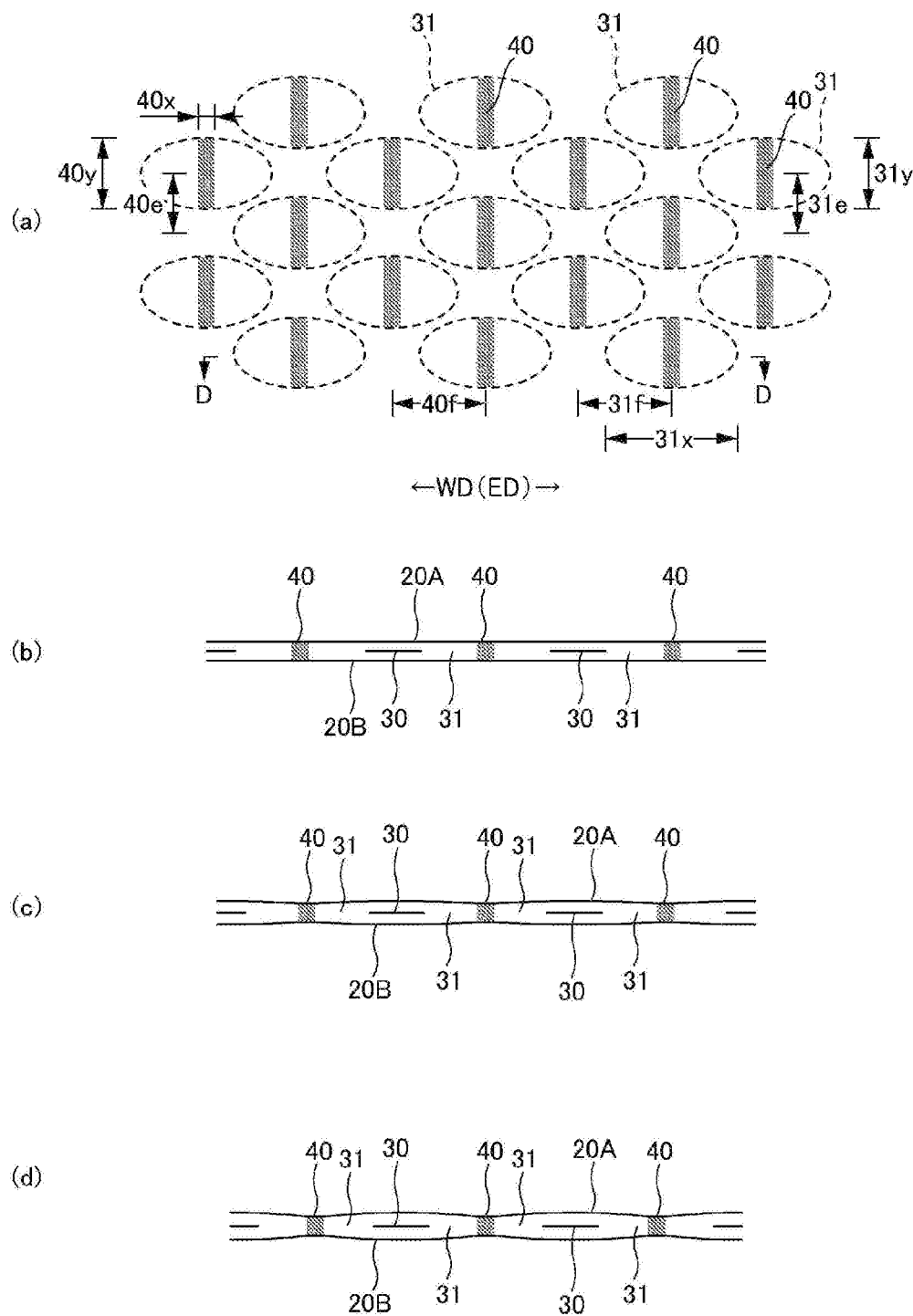
FIG. 13(a) is a plan view of the main part of the outer member.
FIG. 13(b) is a D-D cross-sectional view of FIG. 13(a)
FIG. 13(c) is a cross-sectional view in the worn state.
FIG. 13(d) is a cross-sectional view in the natural length state.
Figure 15:
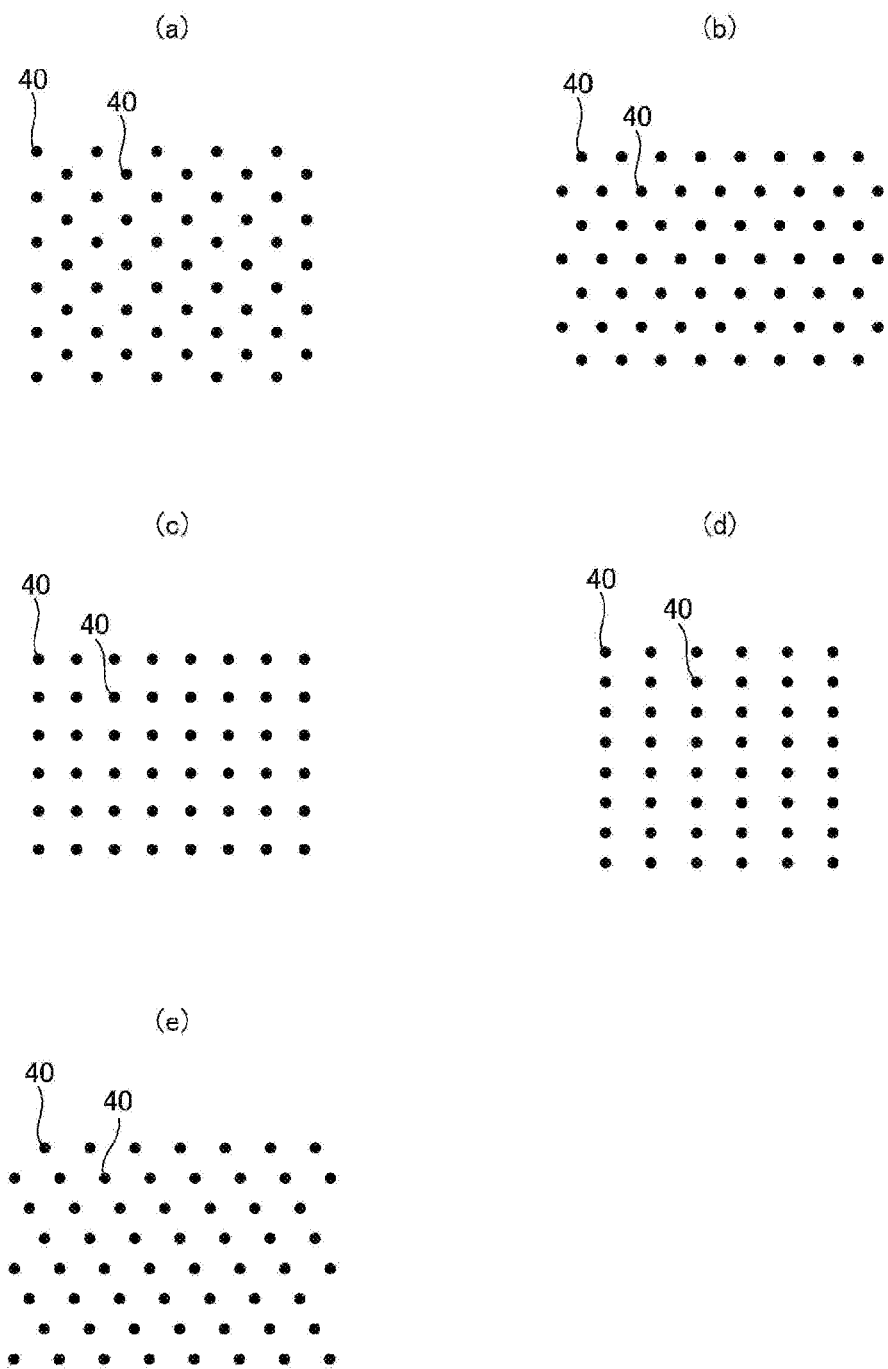
FIG. 15 is a plan view illustrating various arrangement examples of the bonded portions.

An arrangement pattern of the through-holes 31 in the elastic film 30 in the non-stretchable region 70 may be appropriately determined. However, when staggered arrangement is adopted as illustrated in FIG. 13, and a pattern in which a center-to-center interval 31e of the through-holes 31 in the front-back direction LD is shorter than the length 31y of each of the through-holes 31 in the front-back direction LD is adopted, linear continuity in the width direction WD may be almost completely eliminated while maintaining continuity of the elastic film 30, and appearance is preferable as illustrated in FIG. 15. In this case, it is more preferable that a center-to-center interval 31f of the through-holes 31 in the width direction WD is shorter than a length 31x of each of the through-holes 31 in the width direction WD.

In general, especially when stretching stress is in a range of 4 to 12 N/35 mm in stretching the elastic film 30 four times in the width direction WD, in a state in which the non-stretchable region 70 is stretched to the elastic limit in the width direction WD, the center-to-center interval 31e of the through-holes 31 in the front-back direction LD is preferably in a range of 0.4 to 2.7 mm, and the length 31y of each of the through-holes 31 in the front-back direction LD is preferably in a range of 0.5 to 3.0 mm, particularly in a range of 0.7 to 1.1 mm. In addition, the center-to-center interval 31f of the through-holes 31 in the width direction WD is preferably 0.5 to 2 times, particularly 1 to 1, 2 times the length 31y of the through-holes 31 in the front-back direction LD, and the length 31x of each of the through-holes 31 in the width direction WD is preferably 1.1 to 1.8 times, particularly 1.1 to 1.4 times the center-to-center interval 31f of the through-holes 31 in the width direction WD. In a state in which the non-stretchable region 70 is stretched to an elastic limit in the width direction WD (in other words, in a state in which the first sheet layer 20A and the second sheet layer 20B are completely spread), the center-to-center interval 31f of the through-holes 31 in the width direction WD is equal to a center-to-center interval 40f of the sheet bonded portions 40 in the width direction WD, the center-to-center interval 31e of the through-holes 31 in the front-back direction LD is equal to a center-to-center interval 40e of the sheet bonded portions 40 in the front-back direction LD, and the length 31y of each of the through-holes 31 in the front-back direction LD is equal to the length 40y of each of the sheet bonded portions 40 in the front-back direction LD.

In a case in which neither the first sheet layer 20A nor the second sheet layer 20B is bonded to the elastic film 30 in a portion other than a portion between the first sheet layer 20A and the second sheet layer 20B in the sheet bonded portions 40 in the non-stretchable region 70, and gaps, which are generated by the peripheral edge of each of the through-holes 31 of the elastic film 30 and each of the sheet bonded portions 40 separated from each other, are included at both sides of each of the sheet bonded portions 40 in the width direction WD in the natural length state, air permeability is imparted at all times due to the gaps even if the material of the elastic film 30 is a non-porous film or a non-porous sheet, and thus such a case is preferable. In the case of adopting a scheme of simultaneously forming the through-holes 31 and the sheet bonded portions 40 described above, this state is automatically obtained irrespective of a shape of the sheet bonded portions 40, etc.

The shape of each of the sheet bonded portions 40 and the through-holes 31 in the natural length state is not particularly restricted. However, it is desirable to have a small area from a viewpoint of flexibility, and it is desirable to have a shape which is long in the front-back direction LD to eliminate linear continuity in the width direction WD of the elastic film 30. Thus, it is preferable to adopt an ellipse which is long in the front-back direction LD, a rectangle, the rhombus, the convex lens shape, and the concave lens shape. However, when corners are acute as in the rhombus, the elastic film 30 is easily fractured. In contrast, the convex lens shape is preferable since welding of the sheet bonded portions 40 is stabilized, and the concave lens shape is preferable in that an area may be further reduced.

It is possible to appropriately determine the area rate of the sheet bonded portions 40 and the area of each of the sheet bonded portions 40 in the non-stretchable region. However, in general, ranges below are preferable since the area of each of the sheet bonded portions 40 is small, the area rate of the sheet bonded portions 40 is low, and thus the non-stretchable region 70 is not hardened.

Area of each of sheet bonded portions 40: 0.10 to 0.75 mm$^2$ (particularly 0.10 to 0.35 mm$^2$)

Area rate of sheet bonded portions 40: 4 to 13% (particularly 5 to 10%)

As described above, the elongation at the elastic limit of the non-stretchable region 70 may be changed by the arrangement pattern of the through-holes 31, dimensions of each of the through-holes 31, and the center-to-center interval of the through-holes 31. Therefore, although not illustrated, it is possible to make the elongation at the elastic limit different between a plurality of non-stretchable regions 70.

(Change Region of Area Rate of Bonded Portions in Male-Genitalia-Facing Portion)

Figure 2:
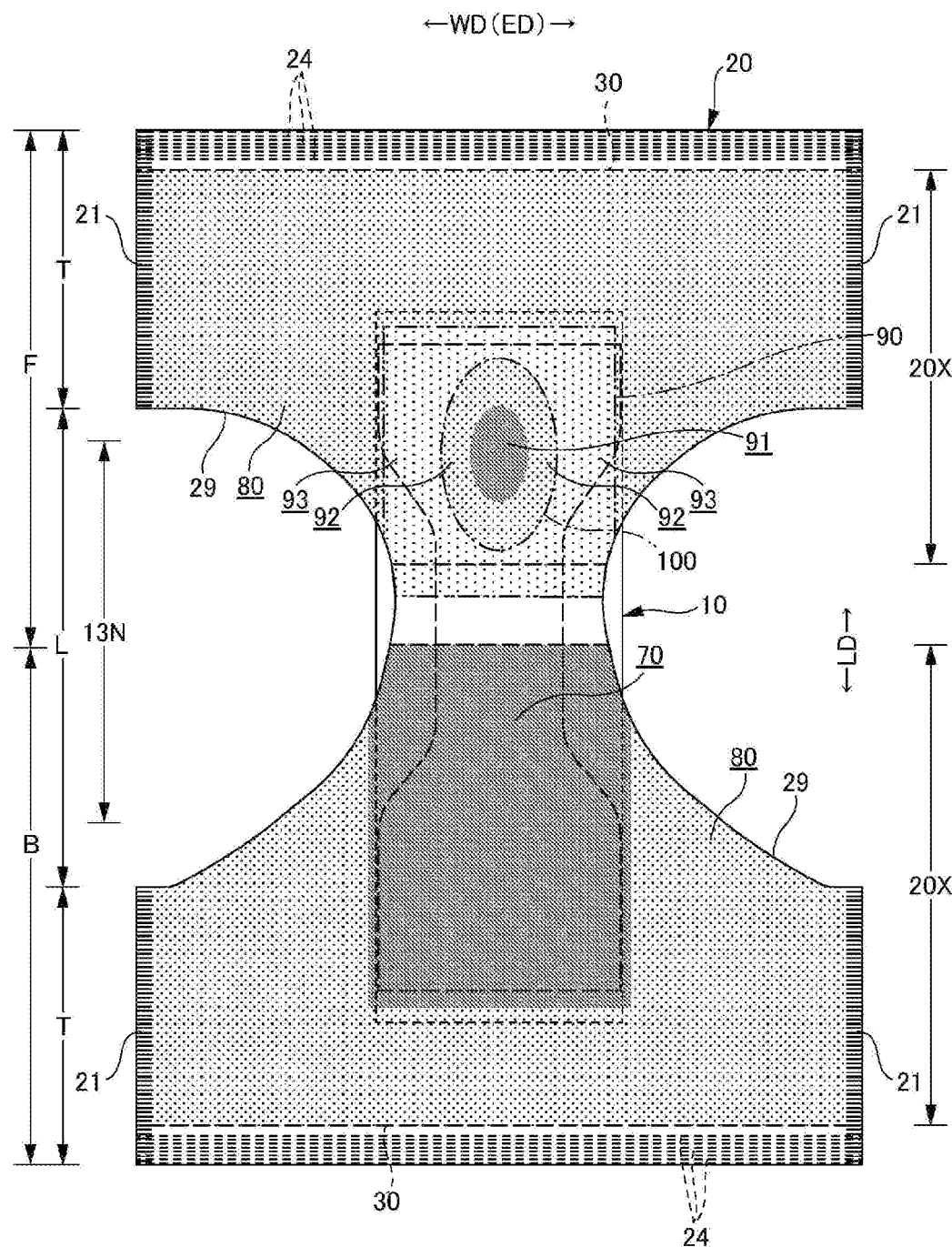
FIG. 2 is a plan view (external surface side) of the underpants-type disposable diaper in the completely spread state.
Figure 3:
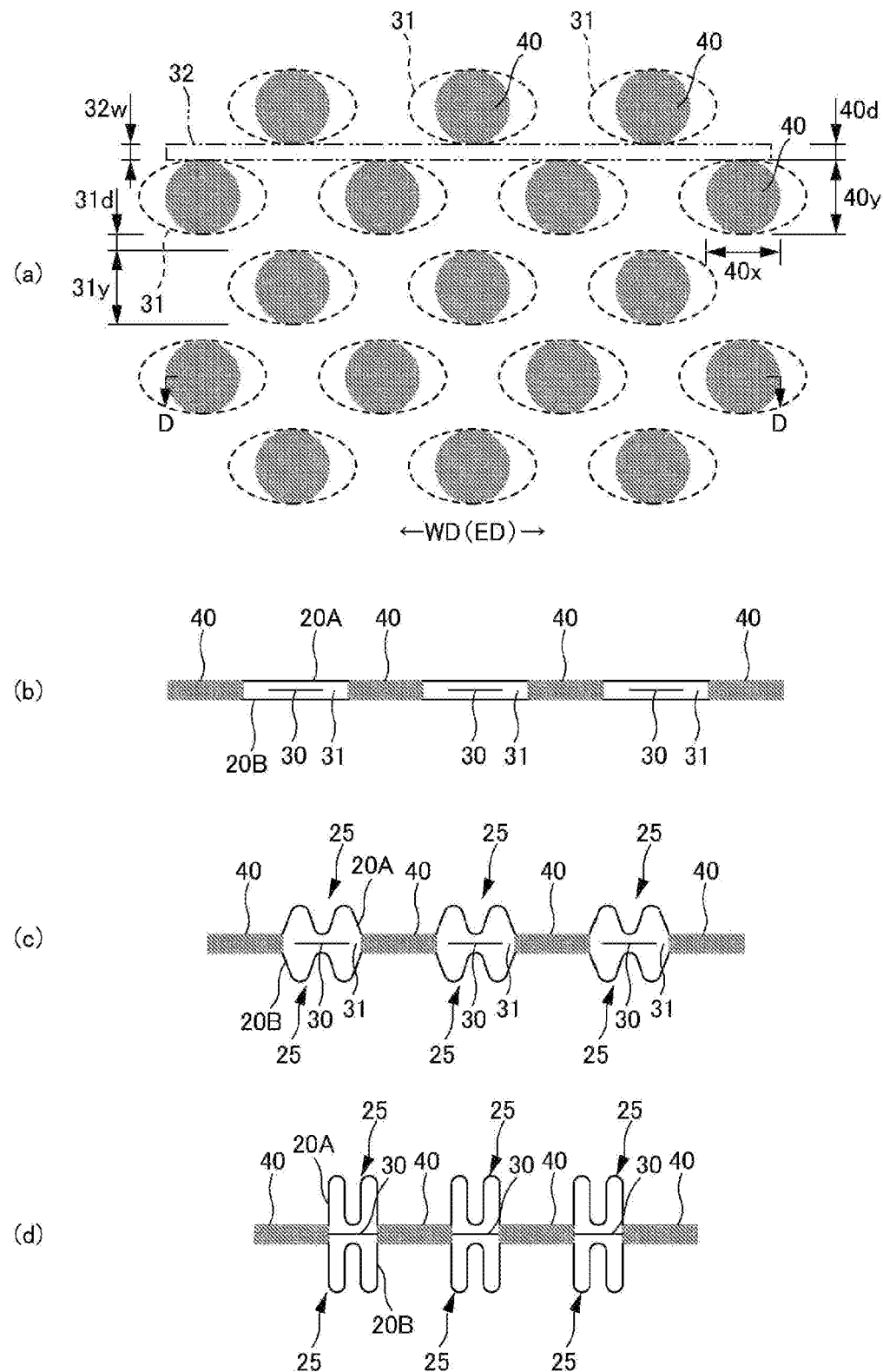
FIG. 3(a) is a plan view of a main part of an outer member.
FIG. 3(b) is a D-D cross-sectional view of FIG. 3(a)
FIG. 3(c) is a cross-sectional view in a worn state.
FIG. 3(d) is a cross-sectional view in a natural length state.

Characteristically, as illustrated in FIG. 2, at least a male-genitalia-facing portion 100 and portions on both sides thereof in the width direction WD in the outer member 20 of the front body F have the elastic film stretchable structure 20X, a change region 90 in which the area rate of the bonded portions 40 decreases stepwise or continuously from a central portion of the male-genitalia-facing portion 100 in the width direction WD to the portions on the both sides of the male-genitalia-facing portion 100 in the width direction WD is included, and at least a portion of the change region 90 other than a portion having the highest area rate of the bonded portions 40, is contracted in the width direction WD due to contraction of the elastic film 30 in the natural length state, and is extensible in the width direction WD. A change in the area rate of the bonded portions 40 is represented by a change in density of a dot pattern in the figure.

In the elastic film stretchable structure 20X as in this mode, basically, as the area rate of the bonded portions 40 increases, a portion in which the first sheet layer 20A and the second sheet layer 20B contract by the elastic film 30 decreases, and elongation at an elastic limit also decreases. Therefore, when the area rate of the bonded portions 40 decreases stepwise or continuously from the central portion of the male-genitalia-facing portion 100 in the width direction WD to the portions on the both sides of the male-genitalia-facing portion 100 in the width direction WD, the male-genitalia-facing portion 100 bulges outward in the natural length state, and bulging is maintained even in the worn state of being stretched to some extent. Furthermore, besides mere bulging, at least the portion other than the portion having the highest area rate of the bonded portions 40 has elasticity, and thus loose-fitting rarely occurs. Therefore, fitting to the male genitalia is remarkably improved.

The male-genitalia-facing portion 100 differs depending on the shape and the dimensions of the product. In a normal case, the male-genitalia-facing portion 100 is located below a center of the front body F in the width direction WD and is a portion within a region overlapping with the inner member 10. As an example, when a waist opening of the front body F is set to 0%, and a center in the front-back direction LD is set to 100%, a range of the male-genitalia-facing portion 100 in the front-back direction LD may be set to a portion within a range of 50 to 100%. Further, when one end in the width direction WD is set to 0%, and the other end is set to 100%, a range of the male-genitalia-facing portion 100 in the width direction WD may be set to a portion within a range of 40 to 60%.

Figure 11:
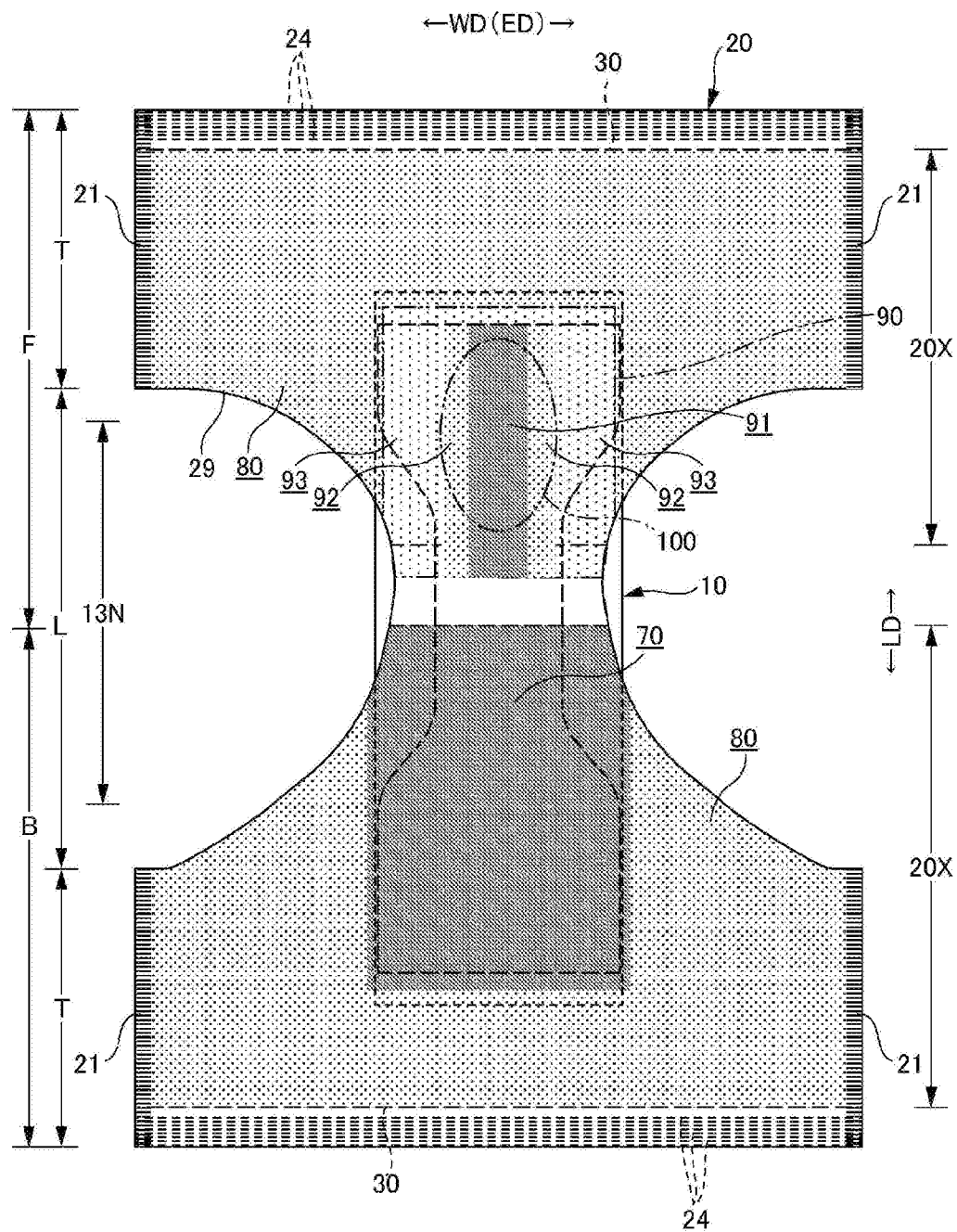
FIG. 11 is a plan view (external surface side) of the underpants-type disposable diaper in the completely spread state.

Even when the area rate of the bonded portions 40 in the change region 90 changes only in the width direction WD as illustrated in FIG. 11, improvement of fitting to the male genitalia can be sufficiently attempted. However, as illustrated in FIG. 2, when the elastic film stretchable structure 20X is provided throughout a range including the male-genitalia-facing portion 100 and a peripheral portion thereof, and the area rate of the bonded portions 40 is decreased stepwise or continuously from the central portion of the male-genitalia-facing portion 100 to the peripheral portion of the male-genitalia-facing portion 100, excellent fitting can be obtained to wrap the whole bulging of the male genitalia.

More specifically, in the mode illustrated in FIG. 11, a region overlapping with the inner member 10 is divided in the width direction WD into three portions corresponding to a portion 91 including the central portion of the male-genitalia-facing portion 100, adjacent portions 92 adjacent to both sides thereof in the width direction WD, and outer portions 93 positioned outside the adjacent portions in the width direction WD, so that the area rate of the bonded portions 40 decreases in three steps.

In addition, in the mode illustrated in FIG. 2, the region overlapping with the inner member 10 is divided into three portions corresponding to a portion 91 including the central portion of the male-genitalia-facing portion 100, an annular portion 92 surrounding the portion (which corresponds to the adjacent portions adjacent to the both sides in the width direction WD, and thus the same reference symbol is used), and a peripheral portion 93 positioned outside the annular portion 92 (which corresponds to the outer portions positioned outside the adjacent portions in the width direction WD, and thus the same reference symbol is used), so that the area rate of the bonded portions 40 decreases in three steps.

In particular, as in the illustrated mode, in a case in which the elastic film stretchable structure 20X is provided throughout a range from a portion on one side to a portion on the other side of the inner member 10 in the width direction WD, when the change region 90 is provided within a range of the inner member 10 in the width direction WD, and an area rate of the portion 93 having the lowest area rate of the bonded portions 40 in the change region 90 is set to be lower than the area rate of the bonded portions 40 in the region 80 outside the change region 90, the amount of contraction increases stepwise or continuously from a central portion of the change region 90 toward the outside thereof and from the outside of the change region 90 toward the change region 90, and fitting to a portion around a bulging portion of the male-genitalia-facing portion 100 is improved, which is preferable. Unlike this scheme, although not illustrated, the portion 93 having the lowest area rate of the bonded portions 40 in the change region 90 may be extended to a wider range and widened to the entire region having the elastic film stretchable structure 20X by the same elastic film 30.

Referring to the area rate of the bonded portions 40, it is possible to attempt sufficient improvement of fitting merely by changing the area rate of the bonded portions 40 in two steps. However, the area rate may be changed in three or more steps as in the illustrated mode. In addition, in the case of the stretchable structure of the elastic film 30 as in this mode, it is possible to change the area rate, that is, the amount of contraction (elongation at the elastic limit) only by the pattern of the bonded portions 40, and thus it is possible to obtain substantially continuous change.

Figure 9:
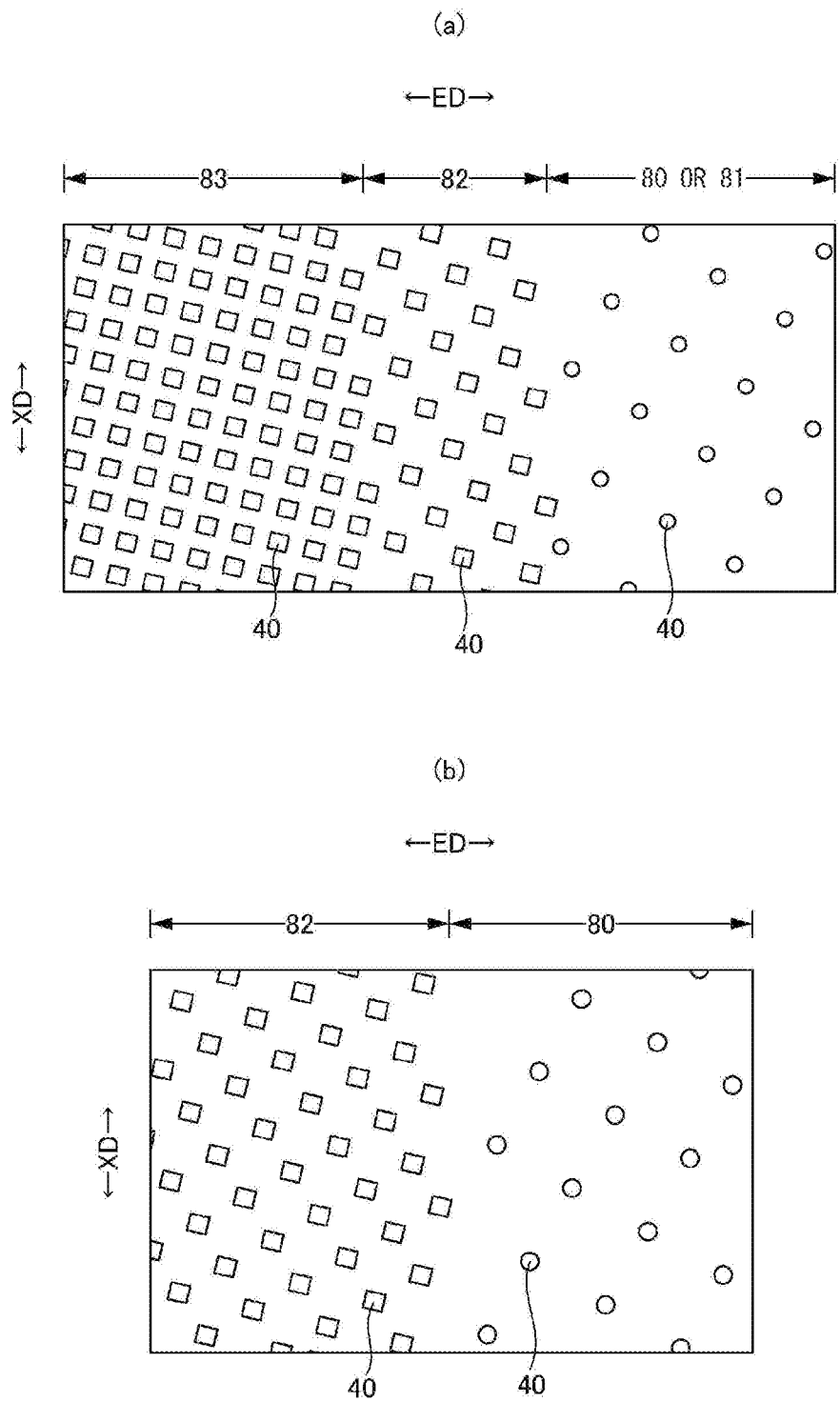
FIG. 9 is a main part enlarged plan view illustrating a pattern of bonded portions.
Figure 10:
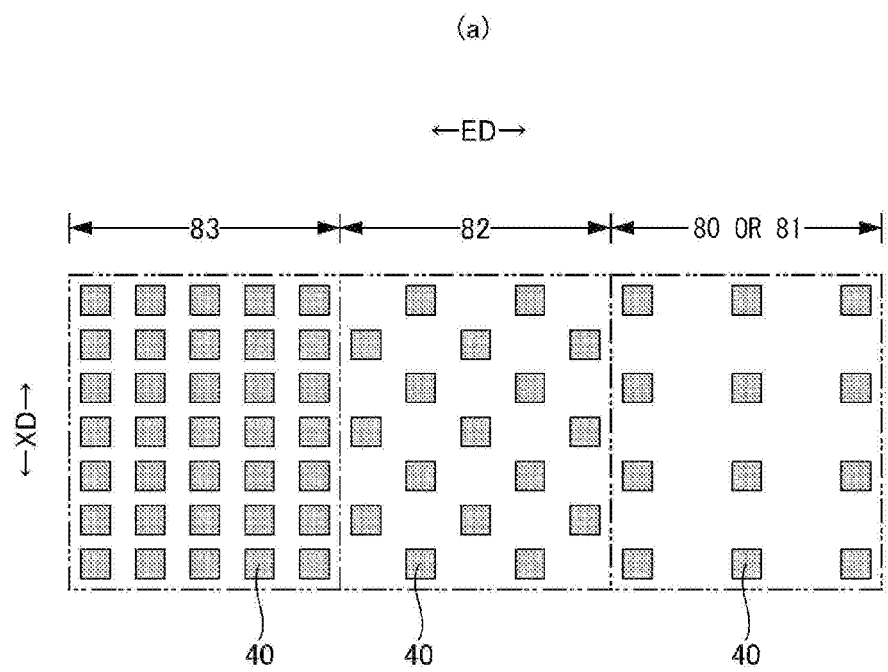
FIG. 10 is a main part enlarged plan view illustrating a pattern of the bonded portions.
Figure 10:
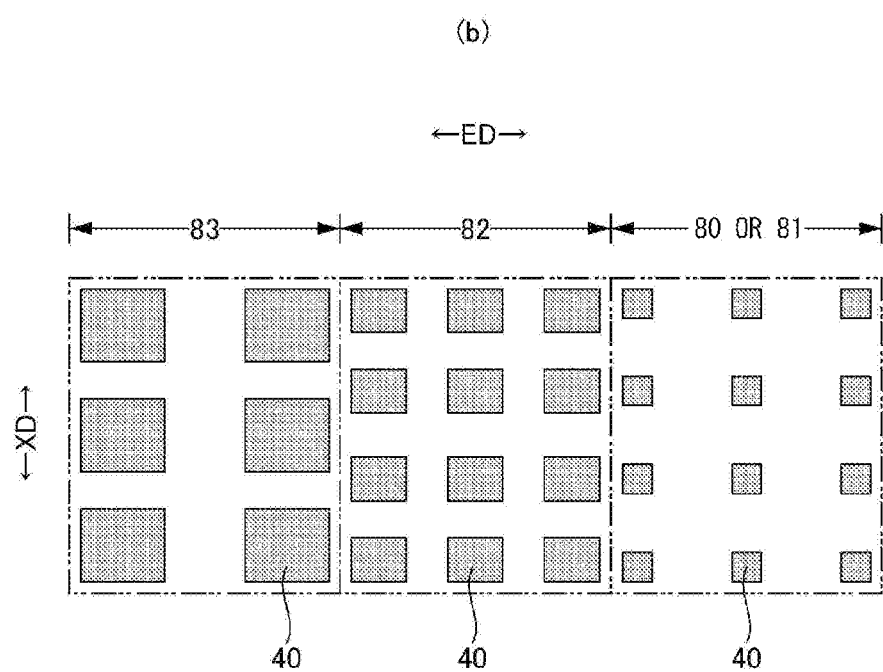

To change the area rate of the bonded portions 40, the number of bonded portions 40 per unit area may be changed as illustrated in FIG. 10(a), or areas of the individual bonded portions 40 may be changed as illustrated in FIG. 10(b). In the former case, areas of the individual bonded portions 40 may be the same or different from each other. In the latter case, the number of bonded portions 40 per unit area may be the same or different. FIG. 9(a) illustrates a pattern example in a case in which the area rate of the bonded portions 40 is changed in three steps, and FIG. 9(b) illustrates a pattern example in a case in which the area rate of the bonded portions 40 is changed in two steps.

The change of the area rate of the bonded portions 40 may be appropriately determined. In a normal case, it is preferable that the change is set to about 9.0 to 13.0% in the central portion of the male-genitalia-facing portion 100 and is decreased therefrom to about 1.9 to 5.0% stepwise or continuously. In particular, in a case in which the area rate of the bonded portions 40 changes in three steps as in the illustrated mode, the change may be set to about 9.0 to 13.0% in the portion 91 having the highest area rate including the central portion of the male-genitalia-facing portion 100, set to about 4.0 to 7.0% in the portion 92 having a medium area rate, and set to about 1.9 to 5.0% in the portion 93 having the lowest area rate. In this case, it is preferable that a difference in the area rate of the bonded portions 40 in the adjacent portion is set to about 2.5 to 5.0%.

In addition, in a normal case, it is preferable that the change in elongation at the elastic limit due to the change of the area rate of the bonded portions 40 is set to less than 130% (more preferably 120% or less) corresponding to the non-stretchable region in the central portion of the male-genitalia-facing portion 100, and is increased to 200% or more therefrom stepwise or continuously. In particular, in the case in which the area rate of the bonded portions 40 changes in three steps as in the illustrated mode, it is possible to set the change to about 100 to 130% in the portion 91 having the lowest elongation at the elastic limit including the central portion of the male-genitalia-facing portion 100, to about 125 to 190% in the portion 92 having the medium elongation at the elastic limit, and to about 200 to 300% in the portion 93 having the highest elongation at the elastic limit. In this case, it is preferable that a difference in elongation at the elastic limit in the adjacent portion is set to about 25 to 100%.

Figure 12:
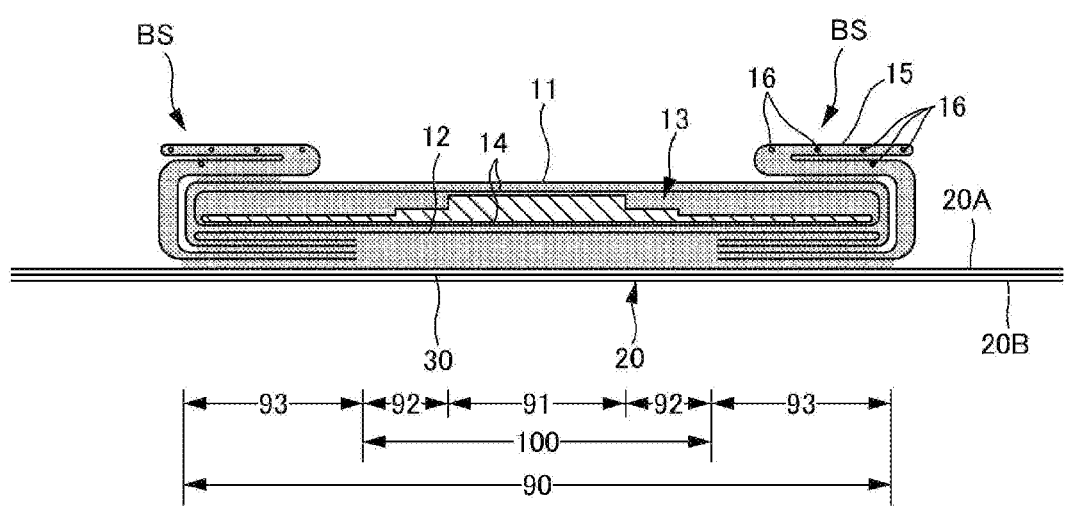
FIG. 12 is a D-D cross-sectional view of FIG. 1.

When a basis weight of a portion overlapping with the change region 90 of the outer member 20 in the absorber 13 is decreased stepwise or continuously (in FIG. 12, a decrease in basis weight is expressed by a decrease in thickness) according to a decrease in the area rate of the bonded portions 40 in the change region 90 as illustrated in FIG. 12 to improve fitting of the male-genitalia-facing portion 100, it is possible to secure a basis weight, that is, the amount of absorption of the absorber 13 without degrading fitting, which is thus preferable. For example, as in the illustrated mode, in a case in which the area rate of the bonded portions 40 decreases in three steps corresponding to the portion 91 including the central portion of the male-genitalia-facing portion 100, the adjacent portions 92 adjacent to the both sides thereof in the width direction WD, and the outer portions 93 positioned outside the adjacent portions 92 in the width direction WD, it is possible to decrease the basis weight of the absorber 13 in three steps in portions overlapping with these portions 91 to 93. A change amount of the basis weight of the absorber 13 may be appropriately determined. However, it is preferable that the change amount is set to about 90 to 100 g/m$^2$ with respect to the area rate 1% of the bonded portions 40. For example, it is possible to set the change amount to 190 to 230 g/m$^2$ when the area rate is 9.0 to 13.0%, to 150 to 180 g/m$^2$ when the area rate is 4.0 to 7.0%, and to 100 to 120 g/m$^2$ when the area rate is 1.9 to 5.0%.

<Others>

The illustrated example is an example in which the elastic film 30 is interposed in the stretchable region 20X, which is provided on the outer member 20 except the waist portion. However, the waist portion elastic members 24 may be omitted by interposing the elastic film 30 up to the waist portion 23, or the elastic film 30 may be overlapped with the waist portion elastic members 24 by interposing the elastic film 30 up to the waist portion 23. In addition, as long as the stretchable region structure 20X of the elastic film 30 is provided at least in the male-genitalia-facing portion 100 and both side portions thereof in the width direction WD, it is possible to impart elasticity by elongated elastic members such as rubber threads without providing the elastic film 30 in other portions. In the illustrated mode, the elastic film stretchable structure 20X is separated into one part of the front body F and the other part of the back body B. However, the structure may be continued from the front body F to the back body B through the crotch portion. Furthermore, the elastic film stretchable structure 20X may be provided only in one of the front body F and the back body B.

Description of Terms in Specification

The terms used in the specification have the following meanings unless otherwise stated.

The "front body" and the "back body" refer to front and back portions using the center of the underpants-type disposable diaper in the front-back direction as a boundary. In addition, the crotch portion refers to a front-back direction range including the center of the underpants-type disposable diaper in the front-back direction, and refers to a front-back direction range of a portion having a narrowing part when the absorber has the narrowing part.

The "elongation at the elastic limit" refers to an elongation at an elastic limit in the stretchable direction (in other words, a state in which the first sheet layer and the second sheet layer are completely spread), and expresses a length at the time of the elastic limit as a percentage when the natural length is set to 100%.

The "area rate" refers to a rate of a target portion to a unit area, and expresses the rate as a percentage by dividing a total area of the target portions (for example, the sheet bonded portions 40, the openings of the through-holes 31, and the vent hole) in a target region (for example, the stretchable region 80, the non-stretchable region 70, a main stretchable portion, and a damping elastic portion) by an area of the target region. Particularly, an "area rate" in a region having a stretchable structure refers to an area rate in a state of being stretched in the stretchable direction to the elastic limit. In a mode in which a large number of target portions is provided at intervals, it is desirable to obtain the area rate by using the target region to a size at which ten or more target portions are included.

The "stretch rate" represents a value relative to the natural length (100%).

The "basis weight" is determined as follows: After the sample or test piece is preliminarily dried, it is allowed to stand in a test room or apparatus under normal conditions (the test location is at a temperature: 20±5° C., relative humidity: 65% or less) until the constant mass. The preliminary drying is to make the sample or test piece be constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is cut from the test piece in the constant mass, with a cutting template (200 mm by 250 mm, ±2 mm). The sample is weighed and the weight is multiplied by 20 into the weight per square meter. The resulting value is defined as the basis weight.

The "thickness" of the absorber is measured using a thickness measurement apparatus of OZAKI MGF Co., Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm$^2$ and a pressurization area of 2 cm$^2$.

The "tensile strength" and the "tensile elongation (elongation at break)" are measured at an initial chuck interval of 50 mm and a speed of testing of 300 mm/min with a tensile tester (for example, AUTOGRAPHAGS-G100N available from SHIMADZU) in accordance with JIS K7127:1999 "Plastics—Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between marked lines) of 50 mm and a speed of testing of 300 mm/min in accordance with JIS K7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AUTOGRAPHAGS-G100N manufactured by SHIMADZU may be used as a tensile tester.

The "spread state" refers to a flatly spread state without contraction or slack.

Unless otherwise specified, dimensions of each portion refer to dimensions in the spread state, not in the natural length state.

In the absence of description about an environmental condition in a test or measurement, the test or measurement is performed in a test room or a device under normal conditions (temperature 20±5° C., relative humidity 65% or less in a test location).

INDUSTRIAL APPLICABILITY

The invention may be used for the underpants-type disposable diaper as in the above example.

REFERENCE SIGNS LIST

B BACK BODY
F FRONT BODY
L INTERMEDIATE REGION
T LOWER TORSO REGION
LD FRONT-BACK DIRECTION
WD WIDTH DIRECTION
ED STRETCHABLE DIRECTION
XD ORTHOGONAL DIRECTION
10 INNER MEMBER
11 TOP SHEET
12 LIQUID IMPERVIOUS SHEET
13 ABSORBER
13N NARROWING PART
14 WRAPPING SHEET
15 GATHER NONWOVEN FABRIC
16 GATHER ELASTIC MEMBER
20 OUTER MEMBER
20A FIRST SHEET LAYER
20B SECOND SHEET LAYER
20C FOLDED PART
20X ELASTIC FILM STRETCHABLE STRUCTURE
21 SIDE SEAL PORTION
24 WAIST PORTION ELASTIC MEMBERS
25 CONTRACTION WRINKLE
29 LEG LINE
30 ELASTIC FILM
40 BONDED PORTION
90 CHANGE REGION
100 MALE-GENITALIA-FACING PORTION

The invention claimed is:

1. An underpants-type disposable diaper comprising:
an outer member disposed in a front body and a back body provided individually or as one unit;
an inner member fixed to the outer member from the front body to the back body, the inner member including an absorber,
side seal portions at which both side edge portions of the outer member in the front body and both side edge portions of the outer member in the back body are bonded together, a waist opening, and a pair of left and right leg openings, wherein
at least a male-genitalia-facing portion and portions on both sides thereof in a width direction, in the outer member of the front body, have an elastic film stretchable structure in which an elastic film is stacked between a first sheet layer and a second sheet layer and the first sheet layer and the second sheet layer are bonded directly or indirectly by a plurality of sheet bonded portions arranged at intervals, and
the outer member of the front body has a change region in which an area rate of the bonded portions decreases stepwise or continuously from a central portion of the male-genitalia-facing portion in the width direction to the portions on the both sides of the male-genitalia-facing portion in the width direction, and at least a portion of the change region other than a portion having the highest area rate of the bonded portions, is contracted in the width direction due to contraction of the elastic film in a natural length state and is extensible in the width direction.

2. The underpants-type disposable diaper according to claim 1, wherein
the elastic film stretchable structure is, in the outer member of the front body, provided at least throughout a range including the male-genitalia-facing portion and a peripheral portion thereof, and
the change region is a region in which the area rate of the bonded portions decreases stepwise or continuously from the central portion of the male-genitalia-facing portion to the peripheral portion of the male-genitalia-facing portion.

3. The underpants-type disposable diaper according to claim 1, wherein the absorber is obtained by mixing and accumulating pulp fibers and superabsorbent polymer particles, and a basis weight of the absorber decreases stepwise or continuously according to a decrease in the area rate of the bonded portions in the change region in a portion overlapping the change region.

4. The underpants-type disposable diaper according to claim 1, wherein the elastic film stretchable structure is provided throughout a range from a portion on one side of the inner member to a portion on the other side of the inner member in the width direction, the change region is provided within a range in a width direction of the inner member, and a lowest area rate of the bonded portions in the change region is lower than an area rate of the bonded portions in a region outside the change region.

5. The underpants-type disposable diaper according to claim 2, wherein the absorber is obtained by mixing and accumulating pulp fibers and superabsorbent polymer particles, and a basis weight of the absorber decreases stepwise or continuously according to a decrease in the area rate of the bonded portions in the change region in a portion overlapping the change region.

6. The underpants-type disposable diaper according to claim 2, wherein the elastic film stretchable structure is provided throughout a range from a portion on one side of the inner member to a portion on the other side of the inner member in the width direction, the change region is provided within a range in a width direction of the inner member, and a lowest area rate of the bonded portions in the change region is lower than an area rate of the bonded portions in a region outside the change region.

7. The underpants-type disposable diaper according to claim 3, wherein the elastic film stretchable structure is provided throughout a range from a portion on one side of the inner member to a portion on the other side of the inner member in the width direction, the change region is provided within a range in a width direction of the inner member, and a lowest area rate of the bonded portions in the change region is lower than an area rate of the bonded portions in a region outside the change region.

8. The underpants-type disposable diaper according to claim 5, wherein the elastic film stretchable structure is provided throughout a range from a portion on one side of the inner member to a portion on the other side of the inner member in the width direction, the change region is provided within a range in a width direction of the inner member, and a lowest area rate of the bonded portions in the change region is lower than an area rate of the bonded portions in a region outside the change region.

* * * * *